US009562210B1

(12) United States Patent
Yamamoto et al.

(10) Patent No.: US 9,562,210 B1
(45) Date of Patent: Feb. 7, 2017

(54) METHODS FOR PRODUCTION OF FATTY ACID ALKANOLAMIDES (FAAAS) FROM MICROALGAE BIOMASS

(71) Applicant: The University of Toledo, Toledo, OH (US)

(72) Inventors: Kana Yamamoto, Toledo, OH (US); Sridhar Viamajala, Toledo, OH (US); Sasidhar Varanasi, Toledo, OH (US); Ajith Yapa Mudiyanselage, Toledo, OH (US); Pramod Prasad Poudel, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/976,662

(22) Filed: Dec. 21, 2015

Related U.S. Application Data

(60) Provisional application No. 62/095,502, filed on Dec. 22, 2014.

(51) Int. Cl.
*C07C 231/00* (2006.01)
*C11B 3/04* (2006.01)

(52) U.S. Cl.
CPC .................................... *C11B 3/04* (2013.01)

(58) Field of Classification Search
CPC .................................................... C11B 3/04
USPC .................................................... 554/66, 69
See application file for complete search history.

(56) References Cited

PUBLICATIONS

Efficient Production of Alkanolamides from Microalgae Ajith Yapa Mudiyanselage, Haoyi Yao, Sridhar Viamajala, Sasidhar Varanasi, and Kana Yamamoto Industrial & Engineering Chemistry Research 2015 54 (16), 4060-4065.*

* cited by examiner

*Primary Examiner* — Deborah D Carr
(74) *Attorney, Agent, or Firm* — MacMillan, Sobanski & Todd, LLC

(57) ABSTRACT

Provided herein are methods for fatty acid alkanolamide (FAAA) synthesis and isolation from lipid-containing algal biomass, and the products of such methods.

26 Claims, 39 Drawing Sheets
(32 of 39 Drawing Sheet(s) Filed in Color)

| TABLE 1 Isolation of FAAAs from Algal Biomass Lipids – Yields[f] | | | | | | | |
|---|---|---|---|---|---|---|---|
| Rxn. Scheme | Solvent/ Reactant | Catalyst | Rxn. Time (min) | Rxn. Temp (°C) | Phase Sep. | Yield (as wt % of lipids in algae) | |
| | | | | | | FAME | FAAA |
| A | EA[a] | none | 90 | 120 | none | – | ~95[e] |
| B | MeOH/EA (4:1) | none | 90 | 90 | turbid | ~47[e] | ~30[e] |
| | MeOH/EA (1:1) | none | 90 | 120 | turbid | Trace amount | ~ 94[e] |
| C | MeOH;[b] EA[c] | Amb.15[b][d] NaOMe[c] | 360[b] 90[c] | 90[b] 120[c] | clean | – | > 99 |

[a] Ethanolamine.
[b] Transesterification step.
[c] Amidation step after phase separation. The reaction required 3h without NaOMe catalyst.
[d] Amberlyst 15.
[e] after extraction into ethyl acetate
[f] Performed with 100 mg biomass containing 31-33 mg of lipid content

FIG. 3 – Table 1

Table 2.
Optimization of reaction conversion from FAMEs to FAAAs[a]

| Entry | Cat.% (w/w-biomass) | Temp. (°C) | Time (h) | FAME (%)[e] | FAAA (%) |
|---|---|---|---|---|---|
| 1 | 5 | 120 | 1.0 | <4 | 87.3 |
| 2 | 5 | 120 | 1.5 | – | >94.7 |
| 3 | 1 | 120 | 1.5 | <17 | <79 |
| 4 | 3 | 120 | 1.5 | – | 83.6 |
| 5[b] | 5 | 120 | 1.5 | trace | 87.3 |
| 6 | 5 | 90 | 15 | 14.3< | >52.6 |
| 7[c] | 0 | 120 | 3.0 | – | 93.0 |
| 8[d] | 5 | 120 | 1.5 | – | 95.1 |

[a] Reaction conditions: The biomass (100 mg) containing 35 mg lipid content (measured as FAMEs), methanol (5 mL/g), and 40 w/w% Amberlyst 15 was heated at 90 °C for 6 h in a sealed GC vial with stirring at 300 rpm. After the phase separation and hexane extraction, the upper layer was treated with ethanolamine (100 mg) and subjected to the indicated reaction conditions.
[b] 50 mg of ethanolamine was used. [c] Performed on 1 g (biomass input) scale.
[d] Performed on 500 mg (biomass input) scale.
[e] Sampled at the reaction time indicated.

FIG. 5 - Table 2

N-(2-hydroxyethyl)tetradecanamide palmitoylethanolamide (4Z7Z,10Z,13Z,16Z,19Z)-N-(2-hydroxyethyl)docosa-4,7,10,13,16,19-hexaenamide

METHODS FOR PRODUCTION OF FATTY ACID ALKANOLAMIDES (FAAAS) FROM MICROALGAE BIOMASS

RELATED APPLICATIONS

This application claims priority to U.S. Provisional Application No. 62/095,502, filed under 35 U.S.C. §111(b) on Dec. 22, 2014, the disclosure of which is incorporated herein by reference in its entirety.

STATEMENT REGARDING FEDERALLY SPONSORED RESEARCH

This invention was made with government support under Grant Number CHE-1230609 awarded by the National Science Foundation, Grant Number 1535803 awarded by the National Sciences Foundation, and Grant Number DE-EE0005993 awarded by the United States Department of Energy. The government has certain rights in this invention.

BACKGROUND OF THE INVENTION

The development of algae-based fuels and products has been attracting interest in recent years, recognizing limitation of petroleum resources and increasing global carbon emissions. Use of microalgae as a renewable feedstock has several advantages. Microalgae are fast-growing, can be cultivated on marginal lands using low quality nutrients and water (e.g., seawater or wastewater), and exhibit high lipid productivities. The economic viability of algal biorefineries can be improved through higher-value products, such as oleochemicals, in addition to fuels. As a general rule of thumb, typical bulk price of most specialty chemicals is ~$3/kg whereas fuels are ~$1/kg.

Fatty acid alkanolamides (FAAAs) are lipid derivatives which are found naturally in plants and animal tissues. Industrially, they are used primarily as biosurfactants or biolubricants. Some alkanolamides have important biological roles such as anti-inflammatory activity, attenuation of pain sensation, pro-apoptotic and anorexic effects. Apart from its biological functions in living tissues, this class of lipid derivatives is used in personal care products, pharmaceuticals, detergents, rust inhibitors, ink formulations, and many other applications. FAAAs are mainly manufactured from vegetable oil with annual global demands estimated at 90,000 tons.

A number of studies have reported conversion of fatty acid triglycerides (FAG) from terrestrial biomass (i.e., vegetable oil) to alkanolamides. In general, FAAA can be synthesized by reacting alkanolamine with a fatty acyl donor, such as free fatty acids, fatty acid chlorides, fatty acid alkyl esters, and fatty acid triglycerides (FAG). Acyl chlorides have been used to deliver FAAA product with sufficient purity for biological studies, but are likely unsuitable for industrial-scale production due to cost and the corrosive nature of the reagents. Fatty acids conversion to FAAA can be accomplished using sodium methoxide catalyst but requires harsh reaction conditions due to ionic salt formation. Milder reaction conditions are conceivable with boron-based catalysts, although these catalysts have not been employed in the context of FAAA synthesis. Use of lipase is also possible for the same transformation at lower temperature and is reported to result in better product quality and color; however, enzyme cost and longevity remain a concern for the biocatalyst approach. Most commonly, direct conversion of FAG to FAAA has been studied using ethanolamine as a solvent and reactant with or without sodium methoxide catalyst. A conversion of FAG to FAAA through fatty acid methyl ester (FAME) has also been reported with analogous reaction conditions and with excellent yields for both steps. All these studies focused on converting FAGs from vegetable oils. However, traditional methods used to recover vegetable oils (FAG) from oil seeds such as mechanical "pressing" are not effective with microalgae due to microscopic size of cells and relatively tough cell walls.

In light of the fact that micro-algae is a more abundant renewable source of FAGs compared to vegetable oils, and it does not compete with food supplies, there is an urgent need for suitable and improved methods for producing biosurfactants and biolubricants from microalgae, that are simpler and cheaper, and that involve milder reaction conditions.

SUMMARY OF THE INVENTION

Provided herein is a concise and efficient procedure for FAAA synthesis and isolation from lipid-containing algal biomass. The methods described herein circumvent solvent-based recovery and purification of FAG or FAME prior to conversion to FAAA, resulting in fewer unit operations. In addition, the methods described herein use recyclable catalysts (e.g., Amberlyst 15) and can be operated under mild conditions (<120° C.). In some embodiments, the methods described herein reliably recover at least 50% and up to >95% of the total lipid in the biomass.

In some embodiments, using one-pot in situ conversion methods, algal lipids are either directly converted to FAAAs or first converted to FAME, which is recoverable as a separate phase; in the latter case, the FAME is converted to FAAA either in a separate step or in situ by reacting with an alkanolamine.

Further provided are methods of isolating the product from the reaction mixture.

Provided is a method of fatty acid alkanolamide (FAAA) synthesis and isolation from lipid-containing algal biomass, where the method involves reacting the lipid-containing algal biomass with an alkanolamine, an alcohol, or a mixture of alkanolamine and alcohol, with or without catalysts, in a reaction solvent to achieve in situ conversion of fatty acyl donors (FADs) in the lipids to FAAA, fatty acid alkyl esters (FAAE), or a mixture of FAAA and FAAE; recovering the FAAA, FAAE, or mixture of FAAA and FAAE from the reaction medium; and converting any recovered FAAE to FAAA by reacting the recovered FAAE with alkanolamine in a second step. In certain embodiments, the fatty acyl donors in the lipids are monoglycerides, diglycerides, triacylglycerides, or free fatty acids. In certain embodiments, the FAAE comprises FAME. In certain embodiments, the FAAA comprises fatty acid ethanolamide (FAEA), fatty acid diethanolamide (FADEA), or fatty acid diisopropanolamide (FADIPA).

In certain embodiments, the reaction solvent is an alcohol, and the in situ conversion of the FAD results in formation of FAAE, the method comprising recovering FAAE as a separate phase, and converting the recovered FAAE to FAAA by reacting the recovered FAAE with alkanolamine. In certain embodiments, the reaction solvent is methanol, and the in situ conversion of the FAD results in formation of fatty acid methyl esters (FAME), the method comprising recovering the FAME as a separate phase, and converting the recovered FAME to FAAA by reacting the recovered FAME with alkanolamine. In particular embodiments, the FAMEs are produced through in situ transesterification by reacting the lipid-containing algal biomass directly with a mixture of methanol and an acid catalyst. In particular embodiments, a recyclable solid-acid catalyst is used in the transesterification step. In some embodiments, the solid-acid catalyst comprises Amberlyst 15. In particular embodiments, the in situ transesterification results in formation of a distinct FAME phase which is recovered and converted to fatty acid ethanolamide (FAEA) by reacting the FAME phase with ethanolamine in the presence of a sodium methoxide (NaOMe) catalyst.

In certain embodiments, a two-step transesterification-followed-by-amidation with alkonalamides, with or without an amidation catalyst, is used to recover algal lipids as FAAA products.

In certain embodiments, the lipid-containing algal biomass comprises the microalgae strain *Schizochitrium limacinum* or *Chlorella Vulgaris*. In certain embodiments, the lipid-containing algal biomass comprises a heteotrophic unicellular alga.

In certain embodiments, the method involves mixing freeze-dried microalgae biomass and Amberlyst 15 with methanol, and heating the mixture at 90° C.

In certain embodiments, following completion of the in situ conversion reaction, an upper layer is separated from a lower phase, and the method further comprises treating the lower phase with hexane to extract out the remaining products, and then recombining the lower phase with the upper phase.

In certain embodiments, the reaction solvent is an alkanolamine and the lipids undergo in situ conversion directly to FAAA, and the method further involves recovering the FAAA from the reaction mixture through selective extraction into an immiscible organic solvent, and isolating the recovered FAAA from the organic solvent through distillation. In particular embodiments, the immiscible organic solvent is ethyl acetate (EtOAc).

In certain embodiments, the reaction solvent is ethanolamine and the in situ conversion is conducted at the mild reaction conditions of 120° C. with a catalyst. In certain embodiments, the reaction solvent is ethanolamine and the in situ conversion is conducted at the mild reaction conditions of 120° C. without a catalyst.

In certain embodiments, the reaction medium is a mixture of alkanolamine and alcohol and the in situ conversion of the FAD in lipids results in formation of a mixture of FAAA and FAAE, with the FAAE undergoing further in situ transformation to FAAA by reacting the FAAE with the excess alkanolamine in the reaction mixture, and the method further involves recovering the FAAE and unconverted FAAE through selective extraction into an immiscible organic solvent, isolating the recovered FAAE and unconverted FAAE from the immiscible organic solvent through distillation, and converting remaining FAAE in the recovered mixture to FAAA in a second step by further reacting the FAAE with alkanolamine. In particular embodiments, the reaction medium is a mixture of methanol and ethanolamine, and the in situ conversion of FADs in lipids results in formation of FAEA or a mixture of FAEA and FAME. In particular embodiments, the immiscible organic solvent is EtOAc, into which FAEA and any unconverted FAME are selectively extracted. In particular embodiments, the reaction solvent comprises a 1:1 mixture of methanol and ethanolamine.

Further provided is a method for fatty acid alkanolamides (FAAA) synthesis and isolating from lipid-containing algal biomass, the method involving converting biomass lipids to fatty acid methyl esters (FAME), recovering crude FAME as a separate phase, and converting the recovered FAME to FAAA. In certain embodiments, FAMEs are produced through in situ transesterification by reacting the lipid-containing biomass directly with a mixture of methanol and catalyst. In certain embodiments, the biomass lipids are converted to FAME through a transesterification, and the recovered FAME is converted to FAAA through amidation. In particular embodiments, a recyclable catalyst is used in the transesterification step. In certain embodiments, the biomass comprises a *Schizochitrium limacinum* or *Chlorella Vulgaris* microalgae strain. In certain embodiments, the biomass comprises a heterotrophic unicellular algae. In certain embodiments, the biomass and Amberlyst 15 are mixed with methanol and heated at 90° C.

Also provided are the products of the methods described.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 3: Table 1, showing the isolation of FAEAs from algal biomass (*Schizochitrium limacinum*) lipids by procedures 1, 2, and 3, which are schematically illustrated in FIGS. 1A, 1B, and 1C, respectively.

FIG. 5: Table 2, showing an optimization of reaction conversion from FAMEs to FAAAs.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Described are methods for synthesizing fatty acid alkanolamides (FAAAs), such as fatty acid ethanolamide (FAEA), fatty acid diethanolamide (FADEA), or fatty acid diisopropanolamide (FADIPA). The methods generally involve either (i) covering fatty acyl donors (FADs) in the lipids of microalgae biomass into fatty acid alkyl esters (FAAE), such as fatty acid methyl ester (FAME), and converting the FAAE into FAAA by reacting it with an alkanolamine, or (ii) converting the FADs in the lipids of microalgae biomass directly into FAAA.

Reactive extraction of FAME from biomass by treatment of algal biomass was first discovered with acidified methanol (containing 5% $H_2SO_4$) at 90° C. for 90 min. FAME produced at the end of this reaction forms a separate light phase distinct from the heavier methanol. While not wishing to be bound by theory, it is now believed that methanol first diffuses into microalgae cells and transesterifies FAG (and other lipids), generating FAME. Once generated, FAMEs form a separate phase after exceeding their solubility limit in methanol.

In Situ Amidation of Algal Biomass

Figures 1A, 1B, 1C:
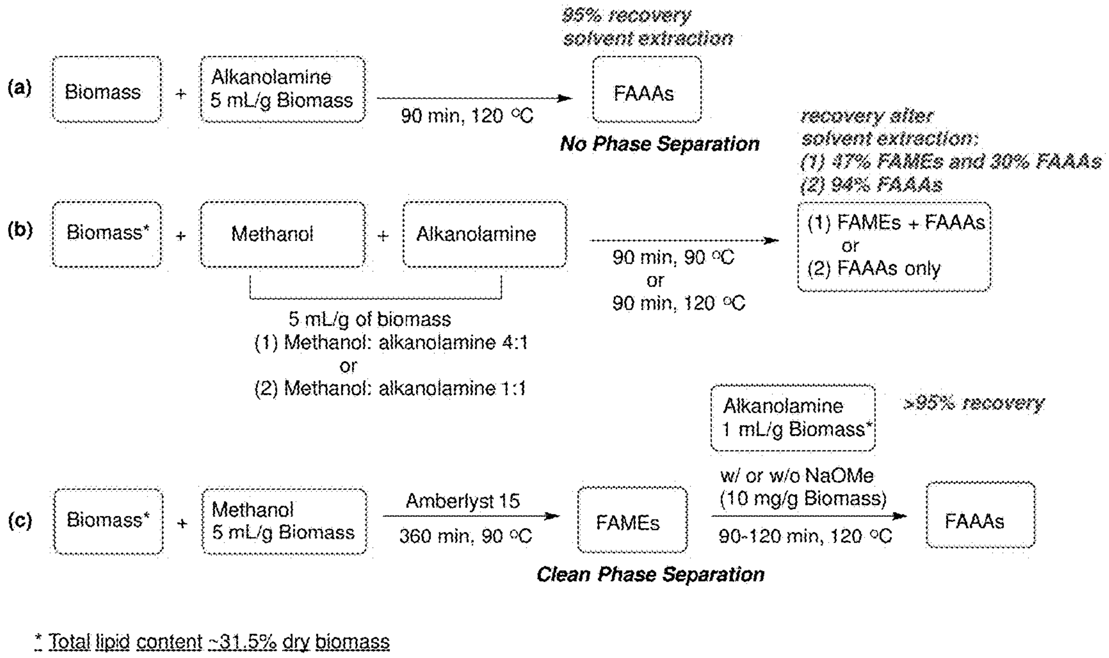
FIG. 1A: Schematic, non-limiting illustration of in situ one-pot production of FAAA from algal biomass lipids. FAAAs are extracted into EtOAc, following in situ amidation of the FAGs in whole algal cells in alkanolamine medium. After isolation, the yields of FAAA were nearly 95%.
FIG. 1B: Schematic, non-limiting illustration of concurrent in situ trans-esterification and amidation of the lipids in whole algal cells, using a mixture of methanol and alkanolamine (AA). FAAAs and FAMEs are extracted into EtOAc, following in situ conversion.
FIG. 1C: Schematic, non-limiting illustration of in situ trans-esterification of algal lipids with methanol, followed by amidation of the FAMEs using alkanolamine to FAAAs in a second-step. Clean phase separation of FAMEs is seen after the first step, and near quantitiative conversion of algal FAGs to FAAAs is seen at the end of the second step.
Figure 2A:
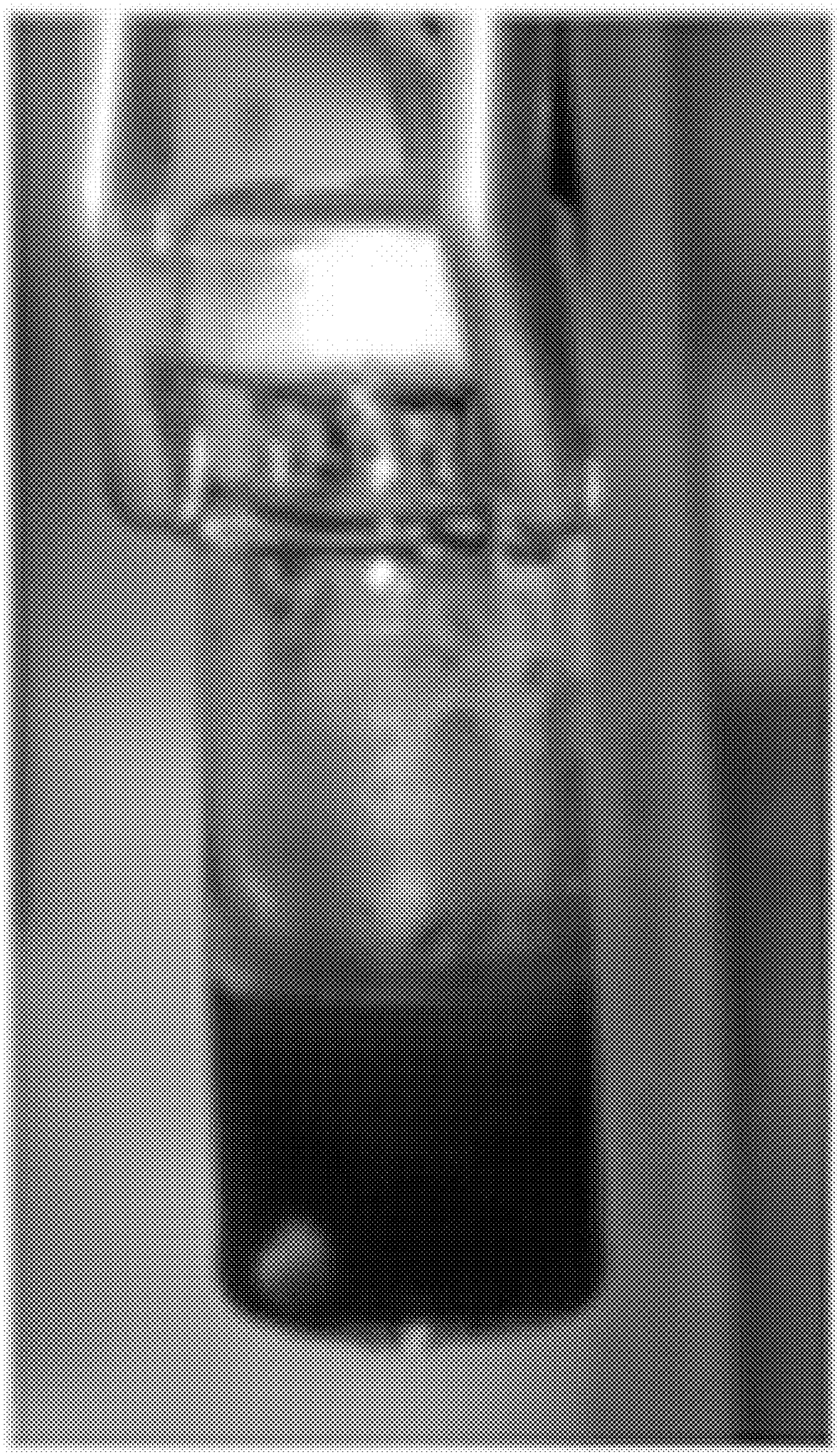
FIG. 2A: Photograph of the reaction mixture, when microalgae strain *Schizochitrium limacinum* and ethanolamine were used, following the completion of the reaction scheme shown in FIG. 1A. Emulsion formation interfered with phase separation of FAEA from the reaction mixture; however, FAEA can be selectively extracted into a solvent immiscible with the reaction mixture.
Figure 9:
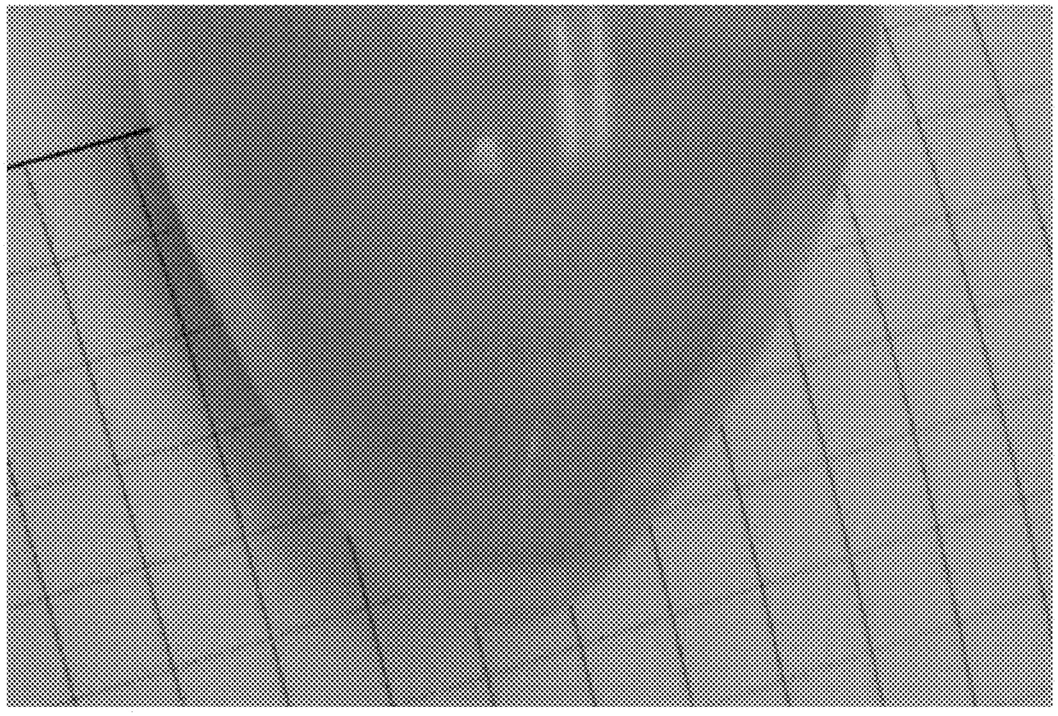
FIG. 9: Crude FAEA extracted with EtOAc from microalgae strain *Schizochitrium limacinum*; after evaporation of the solvent, the FAAA forms a solid film that adheres to the container wall (FIG. 1A, procedure 1).

Efforts began using ethanolamine (EA) as the simplest alkanolamine. Analogously to reactive extraction of FAME, initial efforts on isolation of fatty acid ethanolamide (FAEA) from the biomass were made to directly amidate FAG by treatment of the biomass with alkanolamine with or without sodium methoxide catalyst (FIG. 1A). In general, this procedure led to emulsion formation that resulted in no visible phase separation at 90° C. (FIG. 2A), and the reaction mixture solidified upon cooling to ambient temperature after completion of the reaction. While a distinct phase formation of FAEAs was not observed, in situ conversion of FAGs to FAEAs did take place under these reaction conditions at high yield, as was evident based on the amount of FAEA that selectively extracted from the reaction mixture into the immiscible solvent EtOAc (FIG. 9, FIG. 10, and FIG. 3: Table 1, reaction scheme (A)).

Alkanolamide Synthesis by Concurrent In Situ Transesterification and Amidation

Figure 2B:
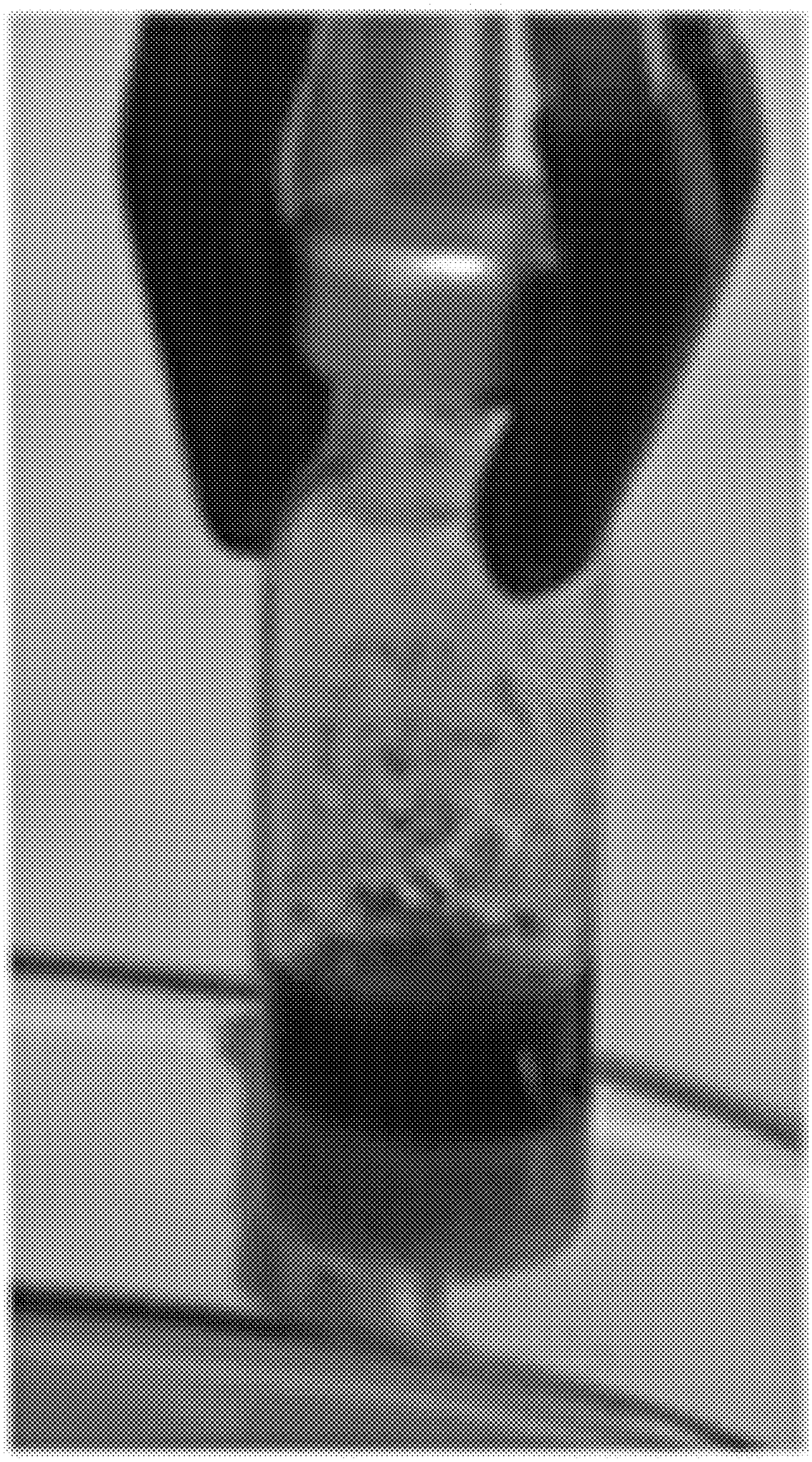
FIG. 2B: Photograph of the reaction mixture, when microalgae strain *Schizochitrium limacinum* was used, following the completion of the reaction scheme shown in FIG. 1B. While there is a discernible phase separation of a mixture of FAMEs and fatty acid ethanolamides (FAEAs) (upper phase) from methanol and ethanolamine (lower phase), isolation of FAMEs and FAEAs still requires the use of an extraction solvent immiscible with the reaction mixture.

In order to assess if supplementation of methanol to the reaction mixture would prevent emulsification of amides and facilitate product phase separation, a reactant mixture comprised of ethanolamine and methanol was used (FIG. 1B and FIG. 3; Table 1, reaction scheme B). Methanol first reacts with FAGs to form a separate FAME layer, and ethanolamine then reacts with the FAMEs to produce FAAAs, with both steps taking place in the same pot. In these experiments, the total amount of mixed-solvent (methanol+ethanolamine) was kept the same as the amount of ethanolamine used in the in situ amidation method, to also reduce usage of ethanolamine (a more expensive chemical relative to methanol) (FIG. 1B). Under these conditions also, nearly quantitative yield of FAAA was achieved (FIG. 11B and FIG. 3: Table 1, reaction scheme (B)), but the reaction formed a turbid mixture (FIG. 2B) at the reaction temperature without discernible phase separation, and solidified at room temperature.

Although FAEA could be recovered through multiple extractions with EtOAc (immiscible to the mixture) in both the in situ amidation procedures described above (FIG. 9 and FIG. 11B), solvent recovery could be energy intense. Therefore, methods that would eliminate the use of solvent, while maintaining near quantitative conversion of biomass lipids to FAEA, were sought.

Two-Step Conversion of Cellular Lipids to FAAA

Figure 2C:
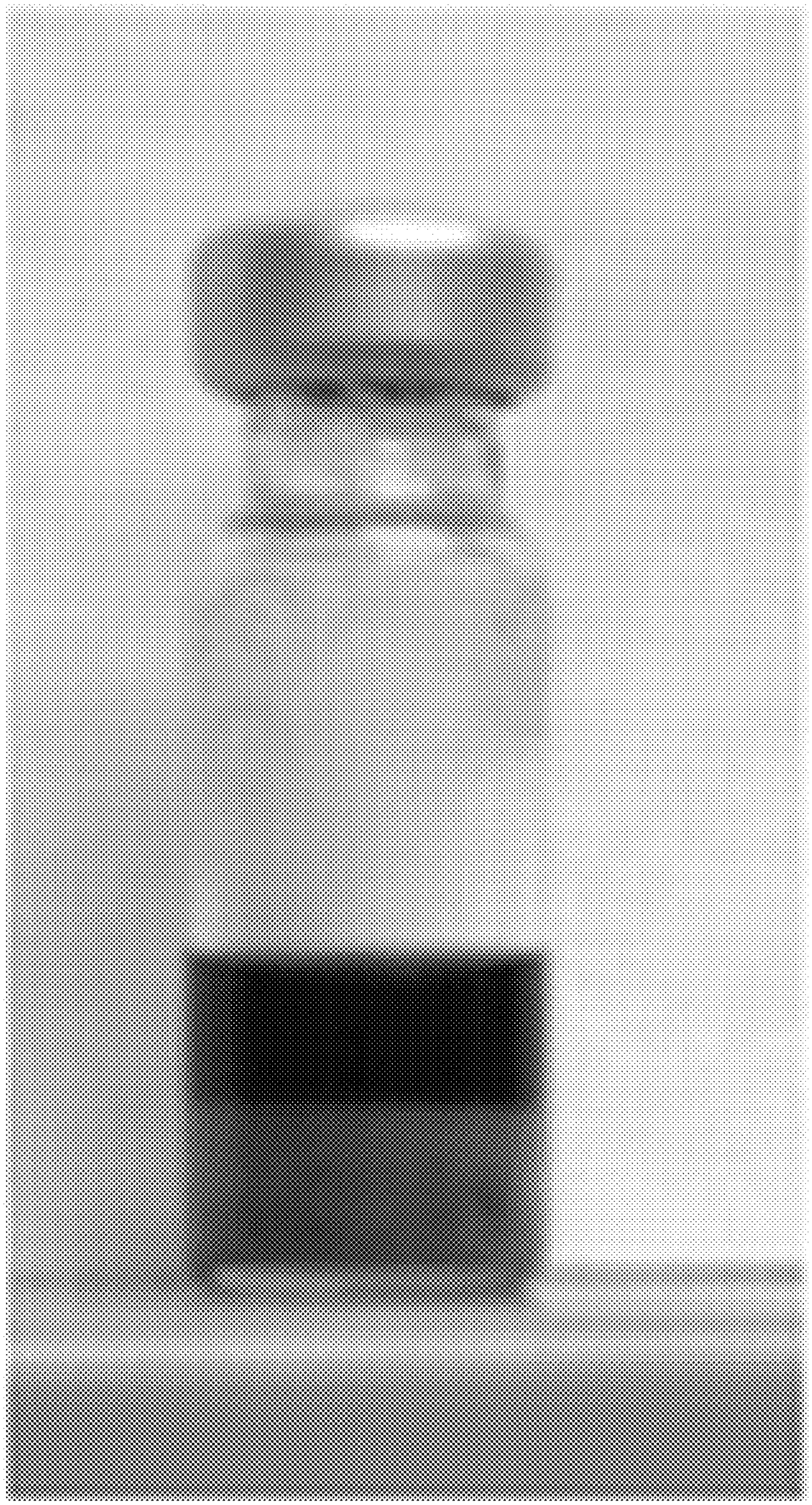
FIG. 2C: Photograph of the reaction mixture, when microalgae strain *Schizochitrium limacinum* was used, following the completion of the first-step of the two-step reaction scheme shown in FIG. 1C. Clear separation of FAMEs (upper phase) and methanol (lower phase) is seen at the end of in situ transesterification step. The separated FAME layer is reacted in a second-step with ethanol amine to form FAEA.

Since the originally established reactive extraction with methanol resulted in near-complete transesterification of cellular lipids and provided an easily separable FAME phase (FIG. 2C), a two-step approach was further pursued. Cellular lipids were recovered as phase-separable FAME in the first step. Subsequently, crude FAME was converted to FAEA in the second step (FIG. 1C). As described below, both steps of this two-step procedure were further optimized giving nearly quantitative recovery of the desired FAEA (FIG. 3-Table 1, reaction scheme (C)).

Figure 4:
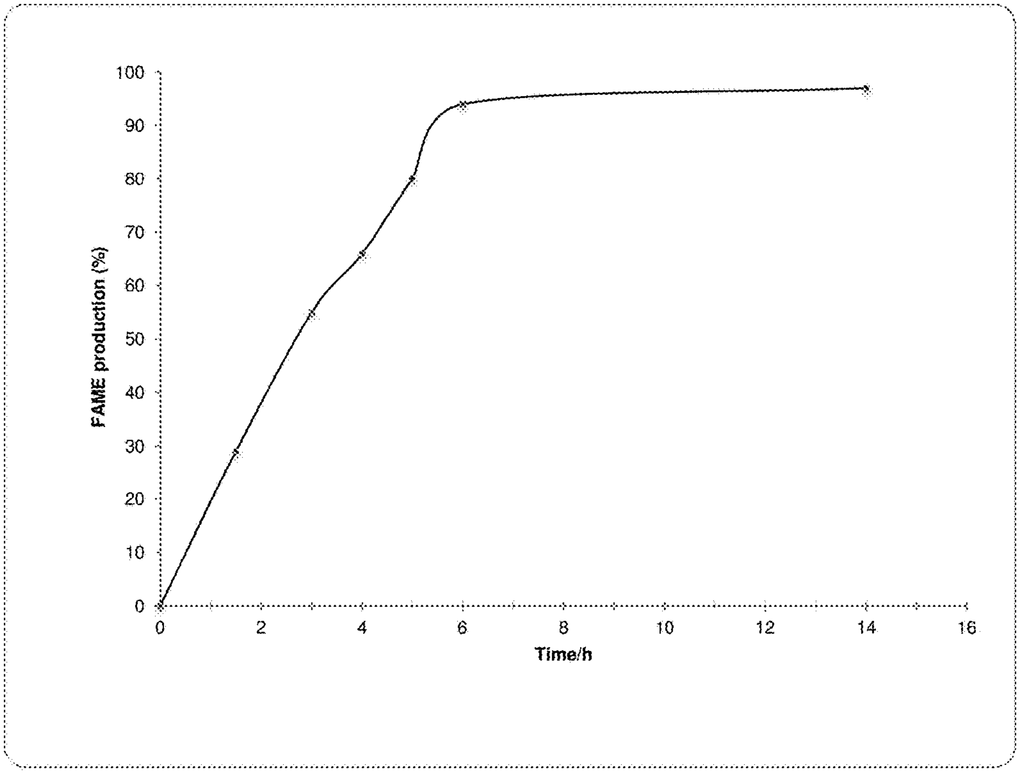
FIG. 4: Kinetics of in situ transesterification of algal lipids (*Schizochitrium limacinum*, lipid content ~31.5%) with Amberlyst 15 catalyst. Reaction conditions: biomass (0.1 g), methanol (0.5 mL), and Amberlyst 15 (40% w/w-biomass). Reactions were carried out in a sealed GC vial at 90° C.

Since removal of residual acid in the first step, as well as catalyst recovery and reuse, is more difficult with homogenous catalysts (such as $H_2SO_4$), in situ transesterification of algal biomass using solid-supported catalysts was pursued. The solid acid catalyst Amberlyst 15 was used for esterification of algal lipids instead of $H_2SO_4$, so that acid can be removed after the first step and the catalyst can be recycled and reused. The transesterification step was optimized first. Reaction conversion was monitored over time for the reaction containing biomass and Amberlyst 15 (40% (w/w-biomass) in methanol (5 mL/g biomass) at 90° C. (FIG. 4). It was observed that the reactions, performed with high concentrations of biomass, produced FAME as a separate phase. To accurately quantify total FAME produced from the reaction, FAME was recovered from both phases after reaction. The upper phase was collected first, and then FAME dissolved in the lower phase was extracted using hexane. The upper phase and solvent extract were combined and solvents were removed under vacuum. From FIG. 4, it can be seen that the reaction completed after 6 h. These experiments show that nearly all of the cellular lipids were obtained as FAME in a single treatment step.

Although hexane extraction was employed to perform quantitative mass balance, in certain embodiments, extraction is not necessary in larger scale operations. Rather, in a continuous process, the methanol phase saturated with FAME including solid catalyst can be recovered after separating out biomass residues. After supplementing with small amounts of fresh methanol (to compensate for consumption during FAME synthesis), the methanol phase can be recycled for subsequent reactions. Because of the high FAME concentration in the recycled methanol, the subsequent reactions will lose only little, if any, FAME to dissolution in the methanol phase. Thus, upon recycle of the methanol media, most, if not all, of the FAME produced in subsequent reactions stays in the upper phase.

Figure 19A:
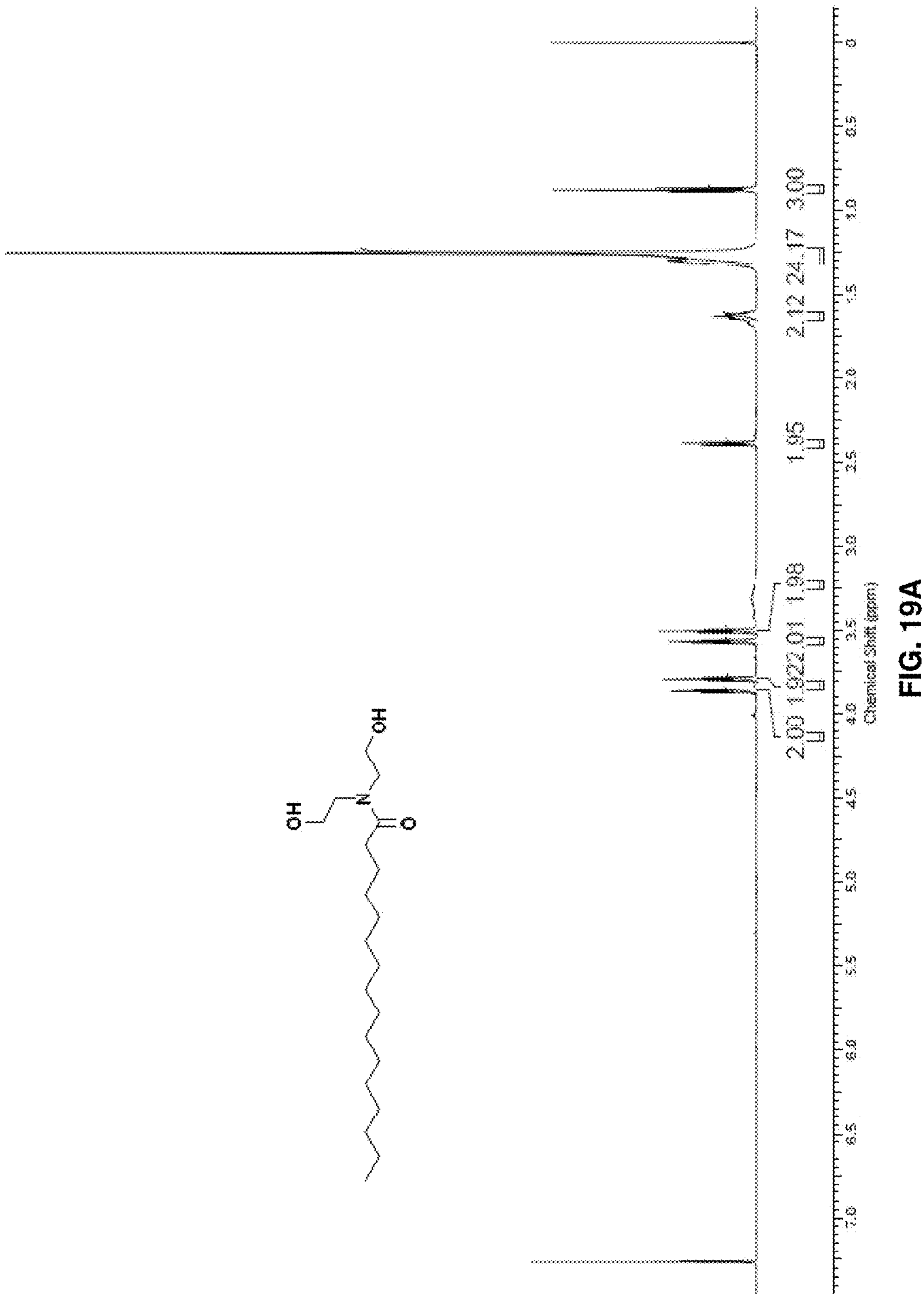
FIGS. 19A-19B: NMR spectra for N-bis(2-hydroxyethyl) palmitanamide—a model FADEA.
Figure 19B:
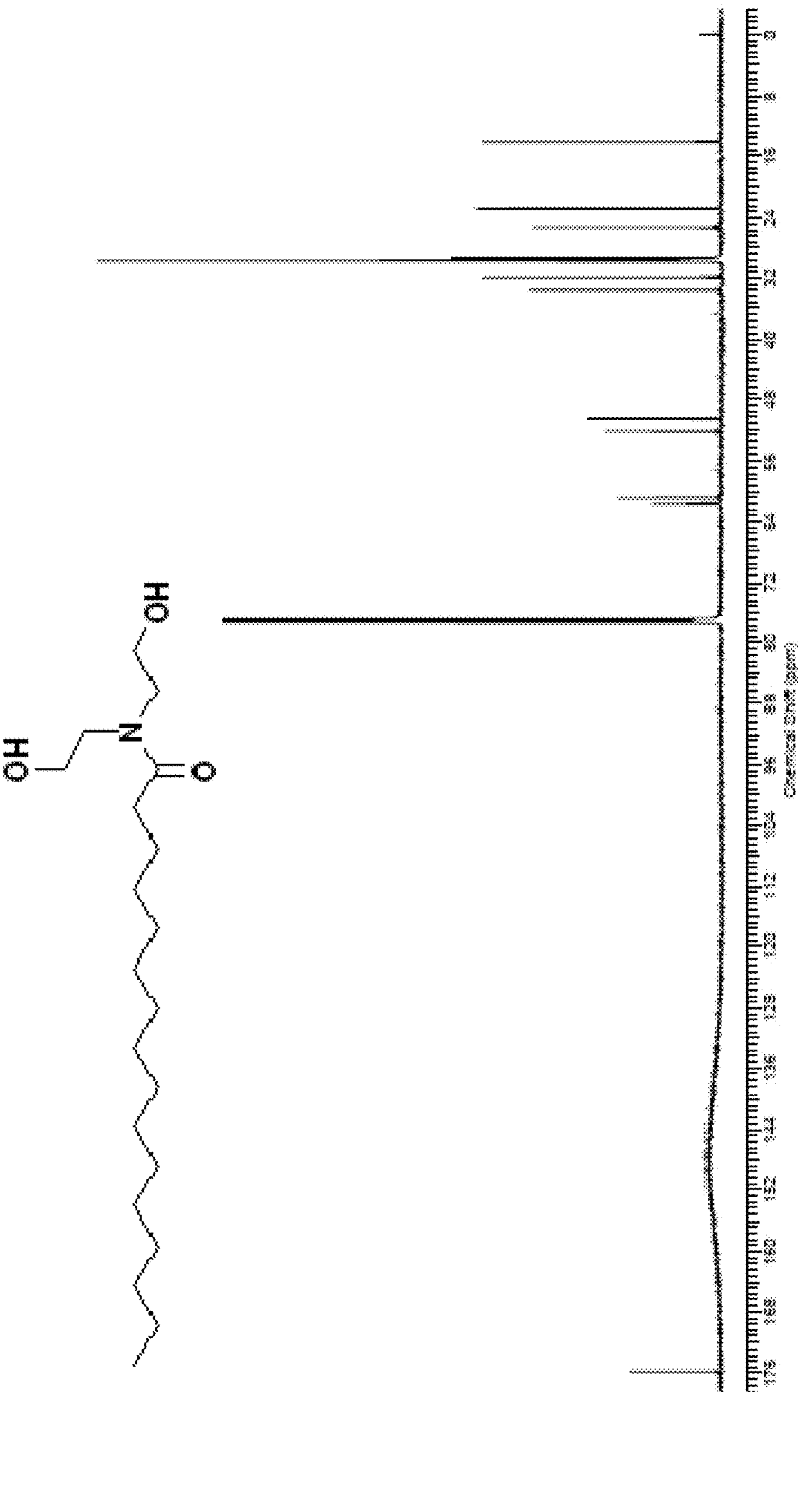
Figure 20A:
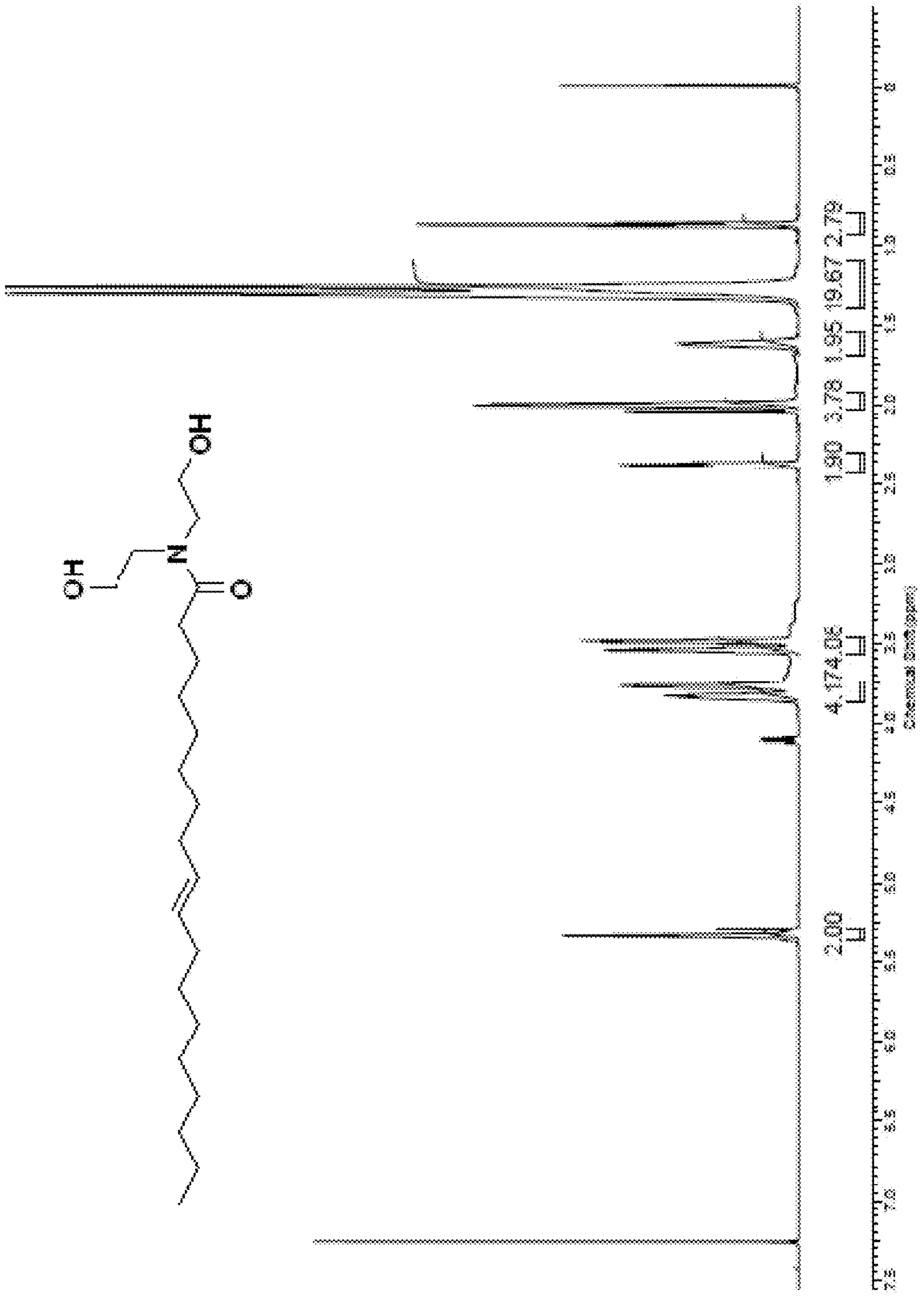
FIGS. 20A-20B: NMR spectra for N-bis(2-hydroxyethyl) oleanamide—a model FADEA.
Figure 20B:
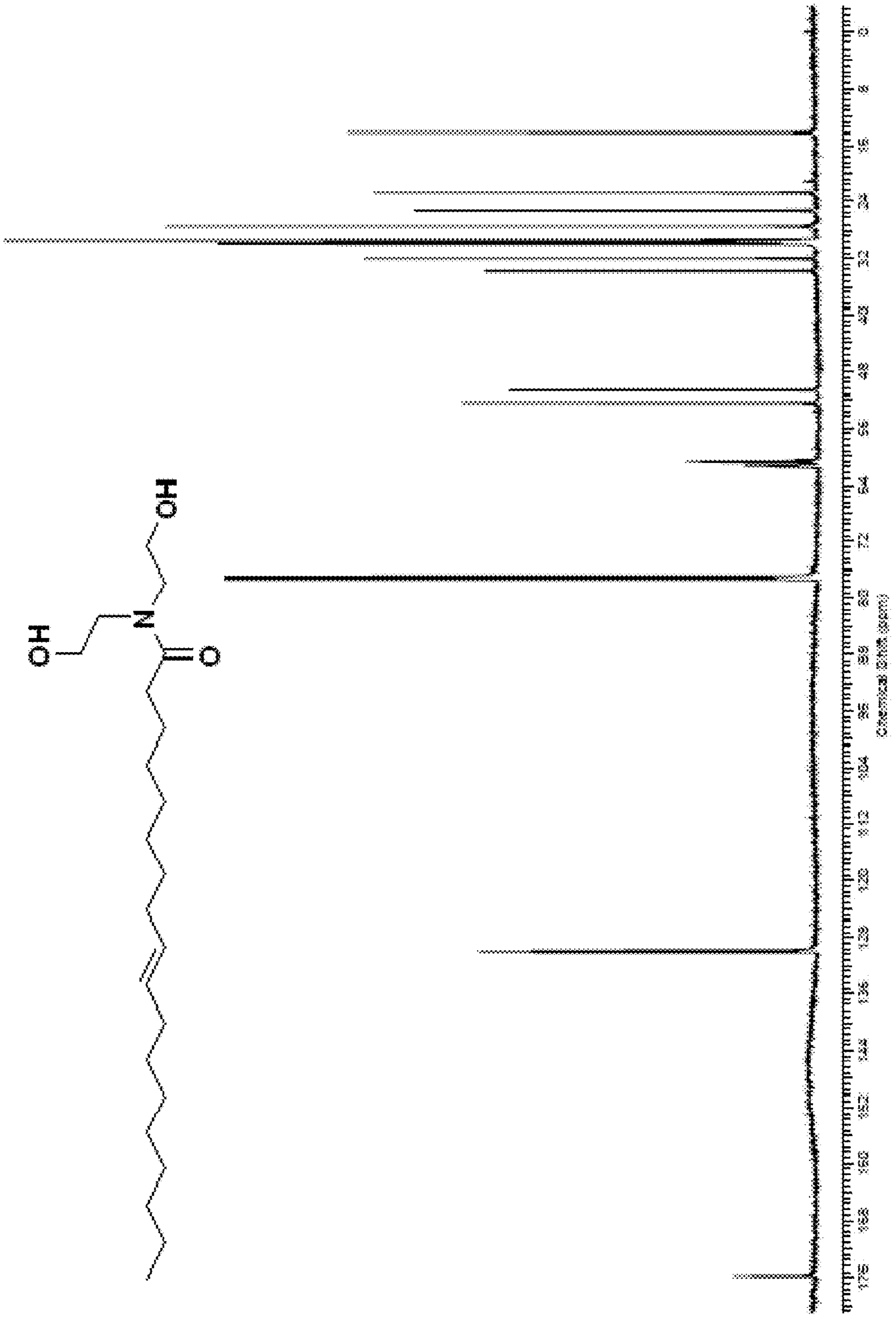
Figure 21A:
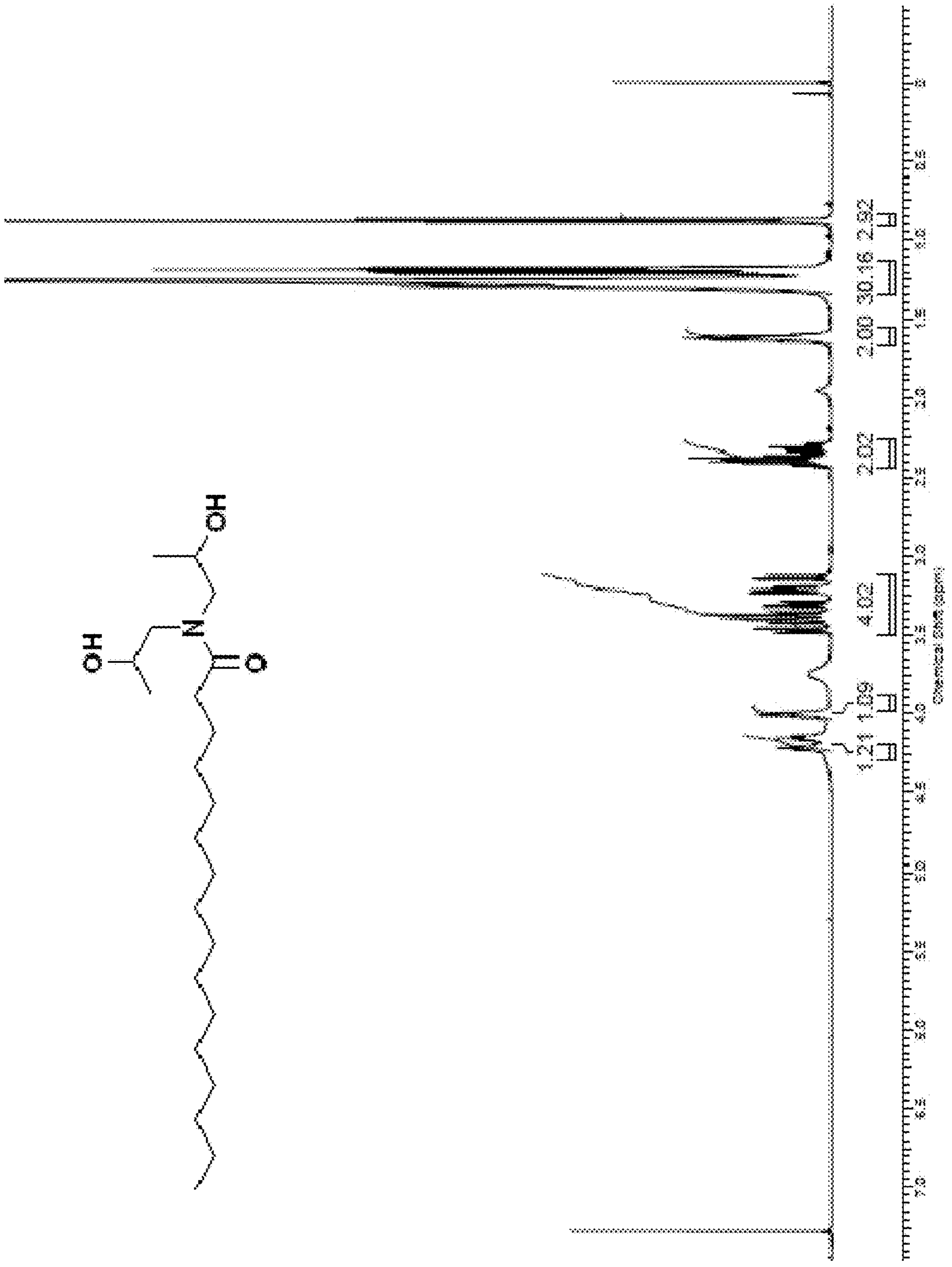
FIGS. 21A-21B: NMR spectra for N-bis(2-hydroxypropyl)palmitanamide—a model FADIPA.
Figure 21B:
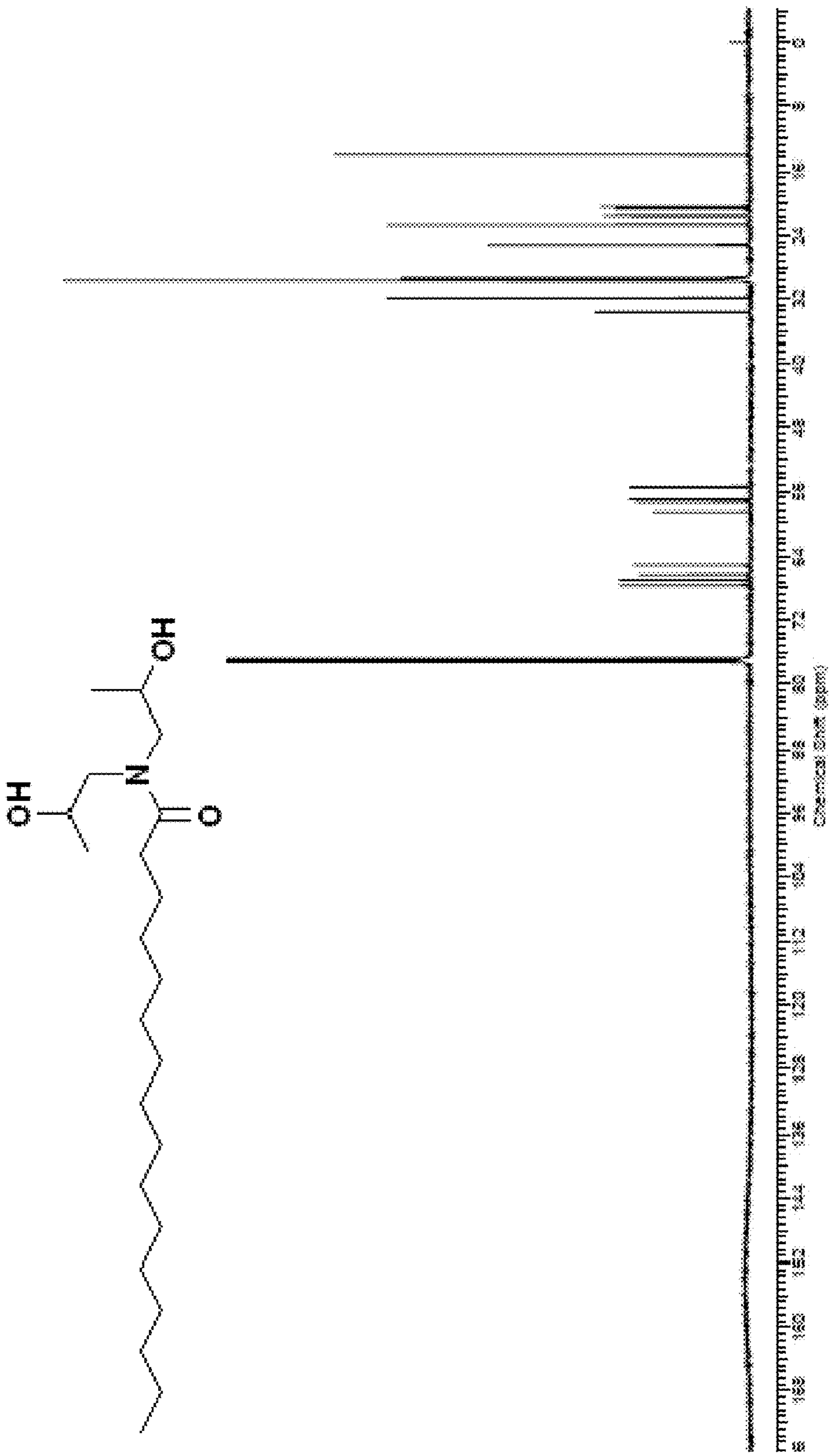
Figure 22A:
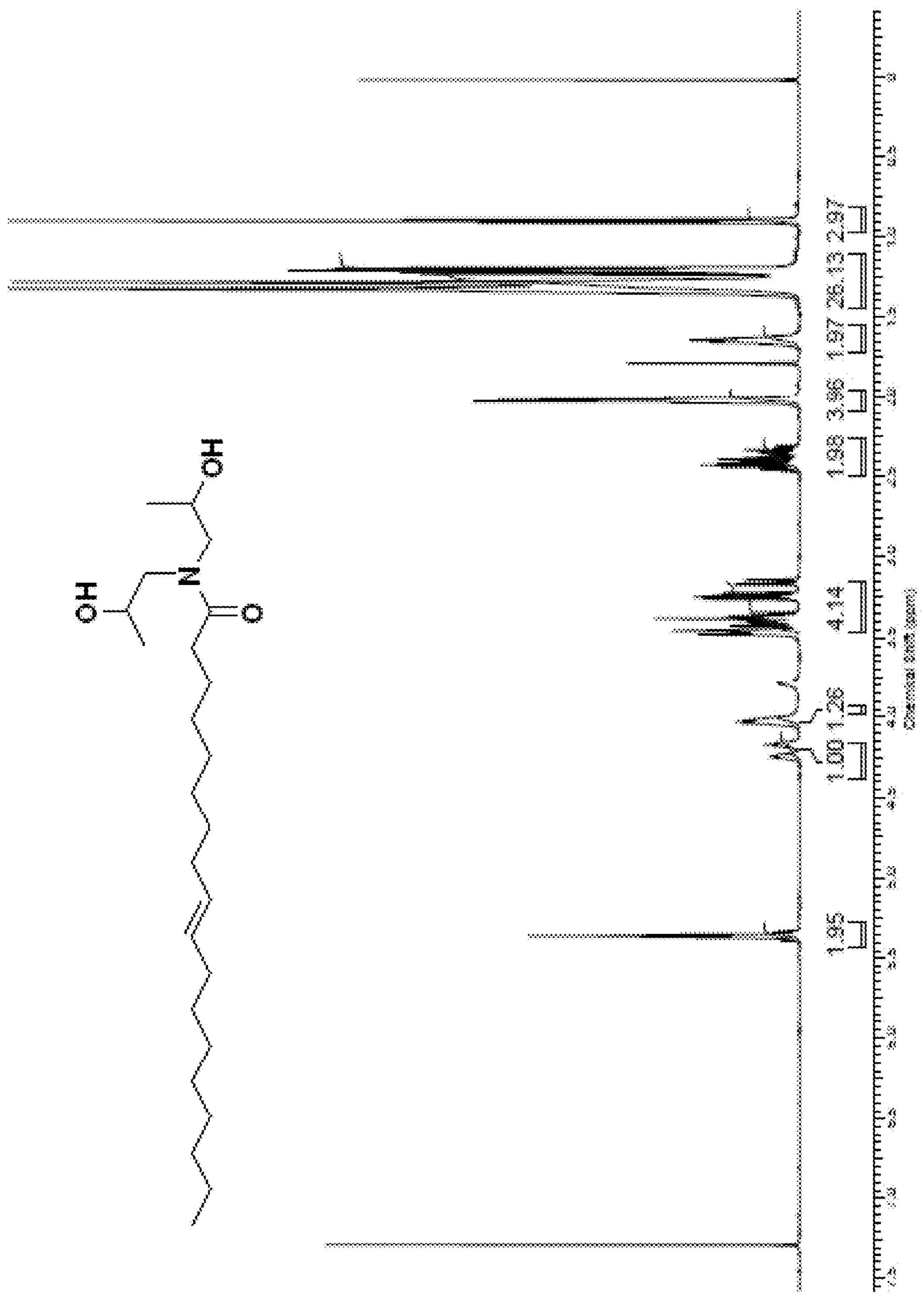
FIGS. 22A-22B: NMR spectra for N-bis(2-hydroxypropyl)oleanamide—a model FADIPA.
Figure 22B:
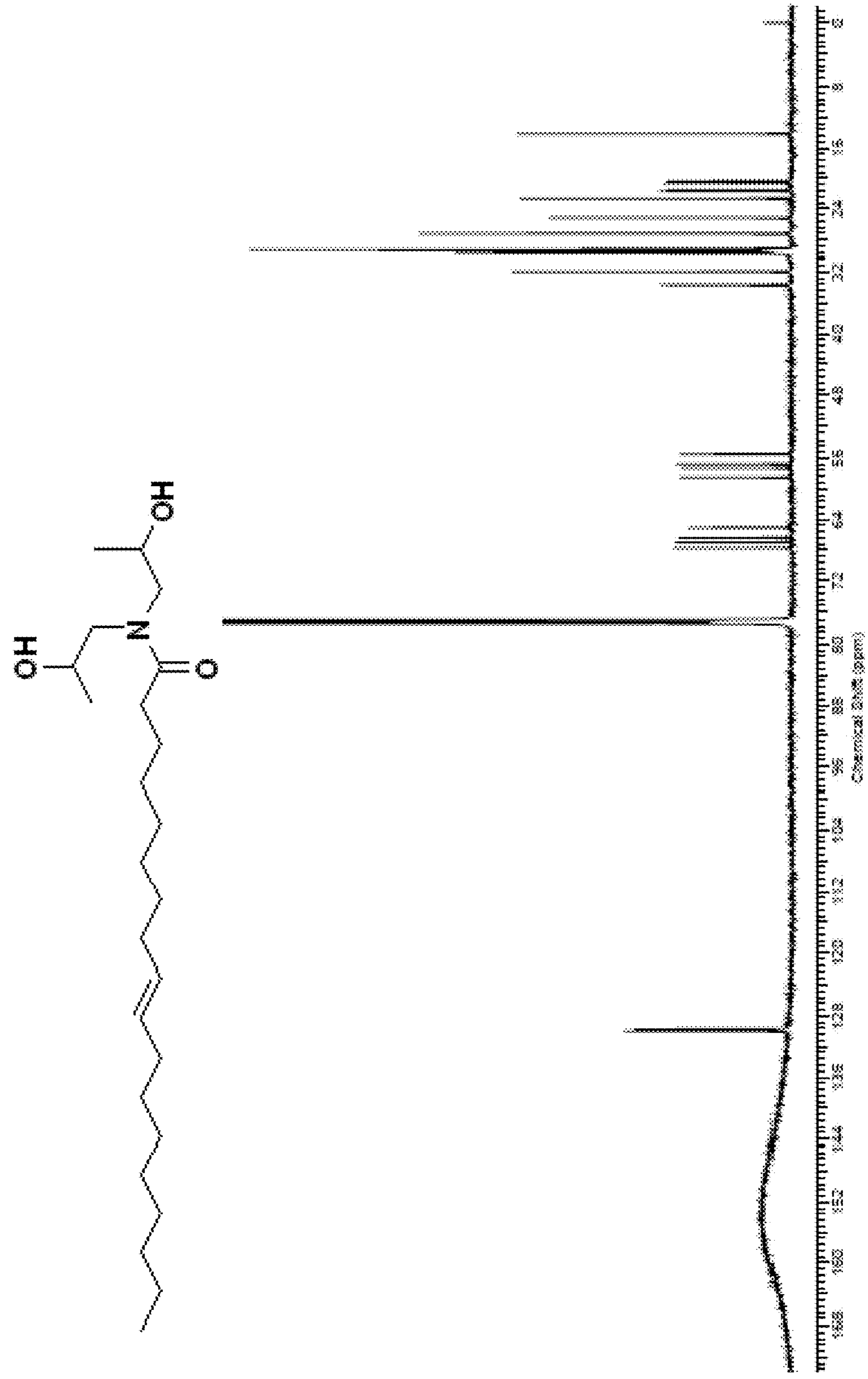
Figure 23:
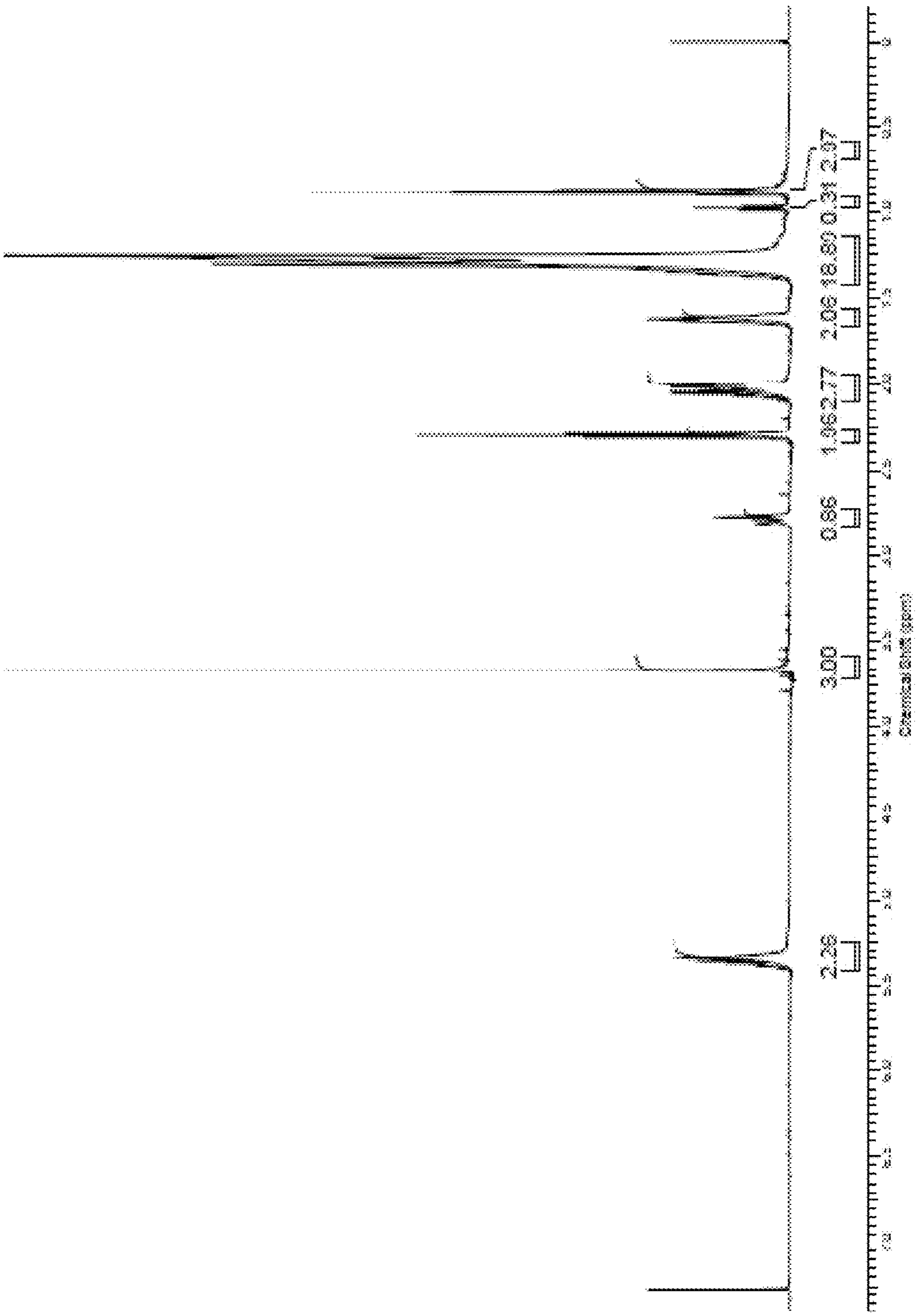
FIG. 23: NMR spectrum of FAME extracted from microalgae strain *Chlorella Vulgaris* in a large scale (85-100 g of dried biomass).
Figure 24:
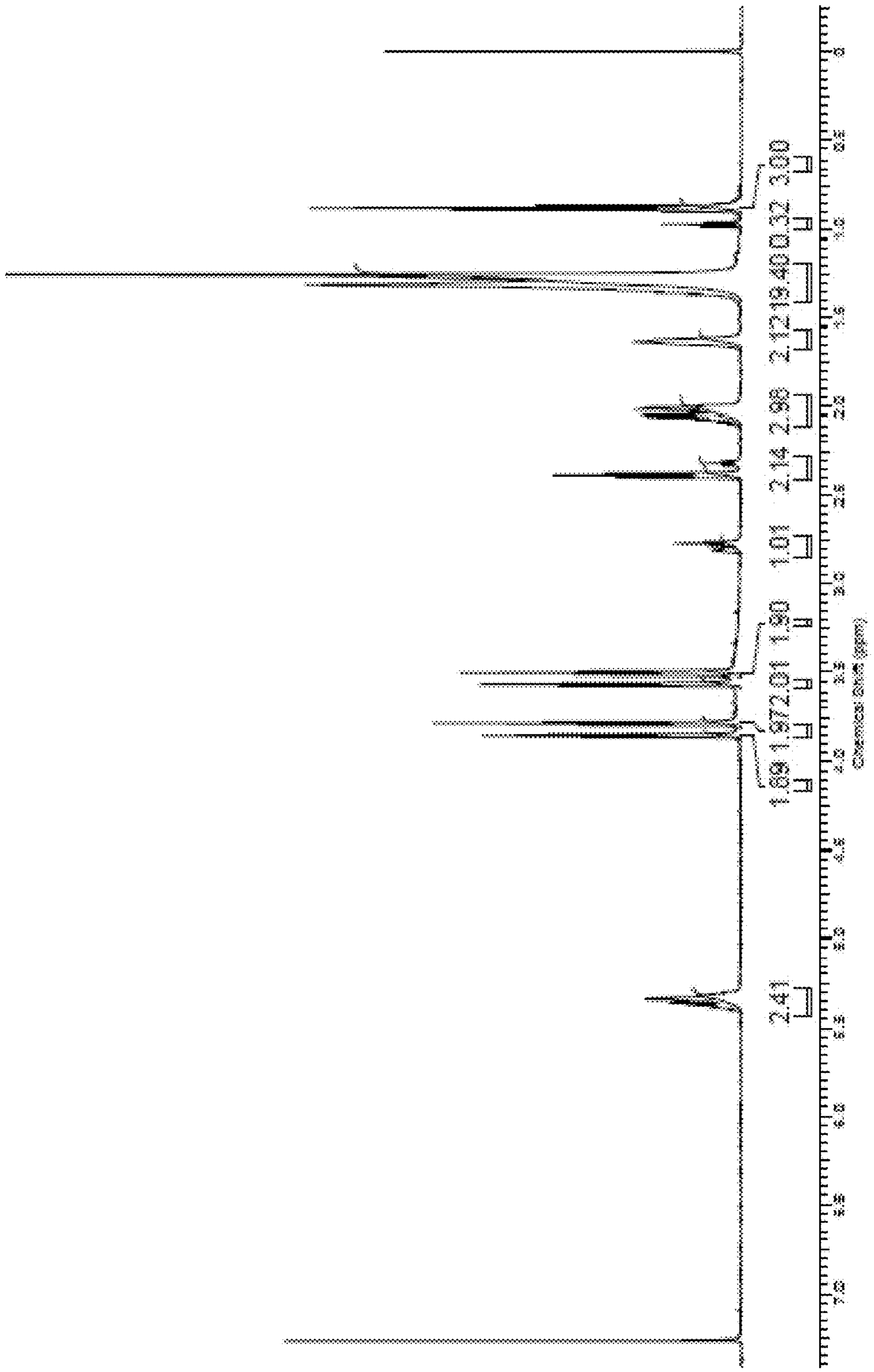
FIG. 24: NMR spectrum of FADEA obtained from microalgae strain *Chlorella Vulgaris* in a large scale (85-100 g of dried biomass).

The upper phase containing FAMEs recovered through this procedure is typically dark brown. The color can be improved by treatment with charcoal (10 w/w %) and subsequent filtration. (FIGS. 19A-19B.)

After recovery, the resulting isolated FAME was treated with ethanolamine (1 g/g biomass, ~10 equiv. of the corresponding FAME) in the presence or absence of sodium methoxide catalyst. With use of 5% (w/w-biomass) sodium methoxide at 120° C., a minimum of 1.5 h was required for completion of the reaction (FIG. 5-Table 2, entries 1 and 2). At 90° C., the reaction did not go to completion even after 15 h (entry 6). Reducing the amount of ethanolamine by half also led to lower product recovery under otherwise identical reaction conditions (entry 5). The possibility of reducing the amount of the catalyst was also tested. At catalyst loadings lower than 5% (w/w-biomass), the reaction conversion and recovery of FAAA were significantly lower under otherwise identical conditions (FIG. 5-Table 2, entries 2 vs 3, 4). However, with extended reaction time (3 h), it was found that the reaction could proceed even without a catalyst (entry 7). It was determined that the optimal reaction conditions for this step are: mass ratio of biomass to ethanol amine 1:1; reaction temperature 120° C.; reaction time 1.5 h (with 5% (w/w) sodium methoxide catalyst) or 3 h (without catalyst). Both procedures (i.e., with and without catalyst) were implemented on gram scale biomass input (entries 7, 8).

Figure 6:
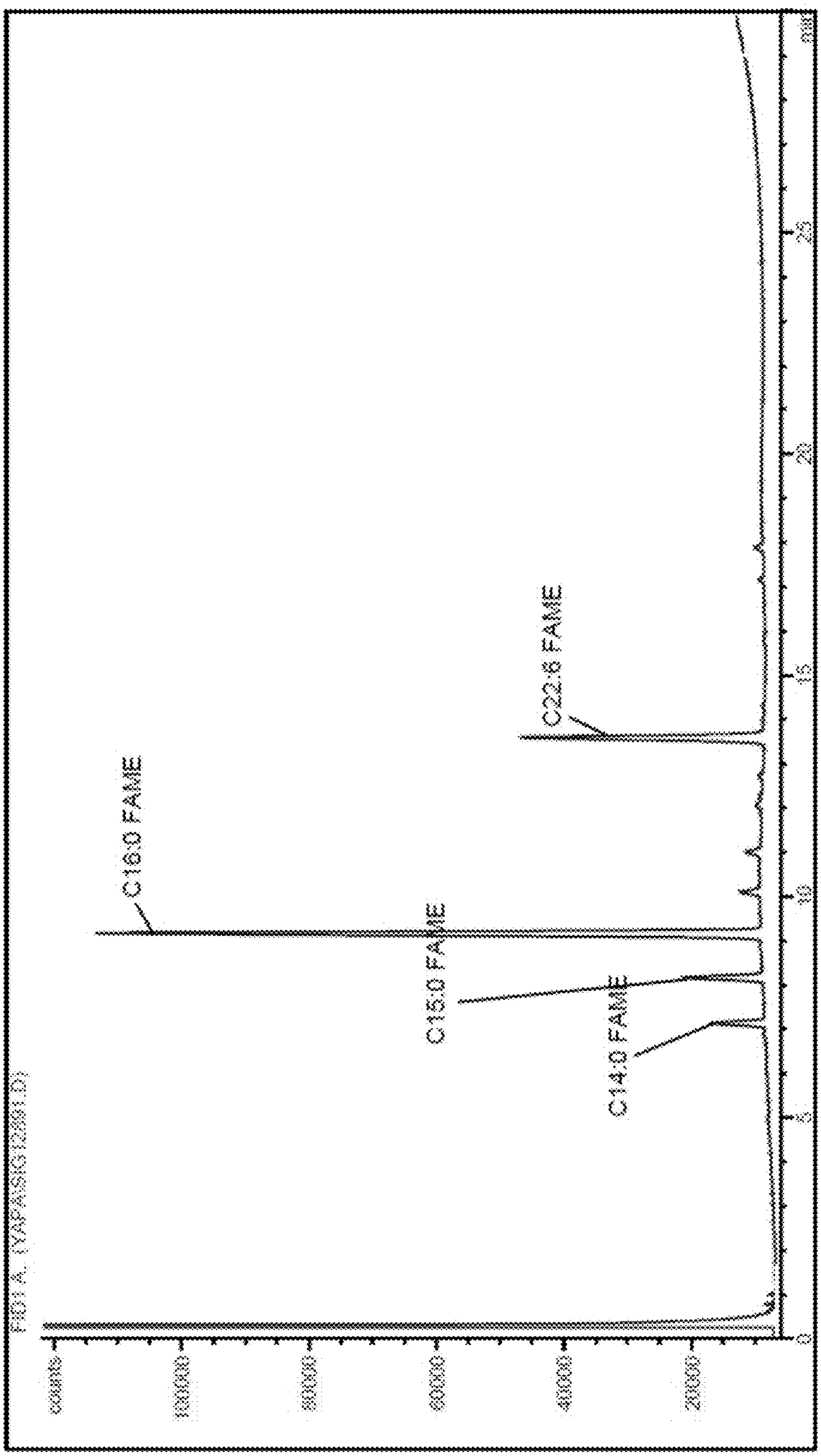
FIG. 6: GC chromatogram of FAMEs isolated from microalgae strain *Schizochitrium limacinum* after transesterification step (FIG. 1C, 3, procedure 3).
Figure 7:
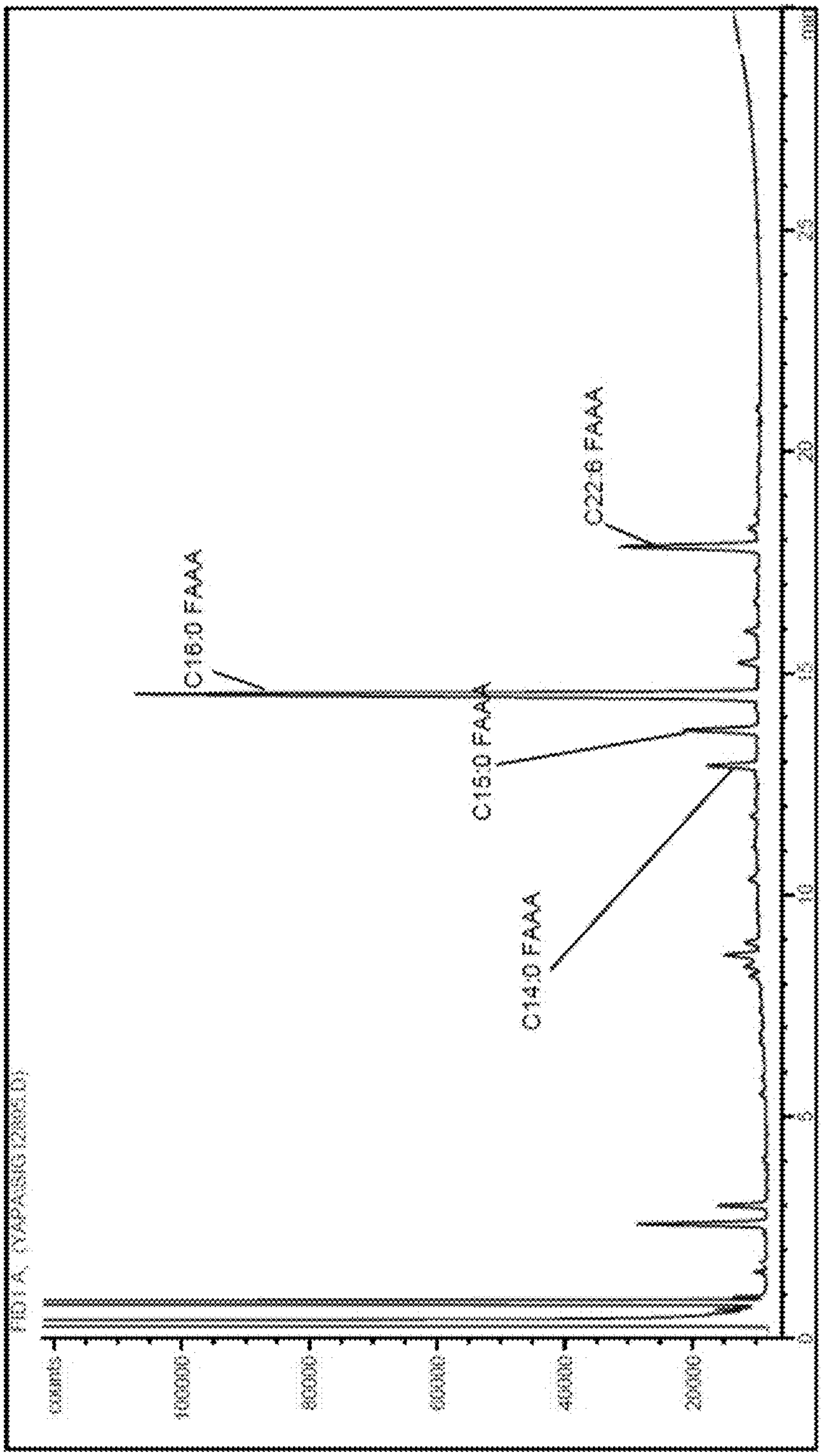
FIG. 7: GC chromatogram of derivatized FAEA isolated from microalgae strain *Schizochitrium limacinum* after amidation step.
Figure 8A:
FIGS. 8A-8B: The typical color of the isolated FAEAs isolated from microalgae strain *Schizochitrium limacinum* was dark brown (FIG. 8A), but was improved after charcoal treatment (10% (w/w-biomass)) and filtration (FIG. 8B).
Figure 8B:
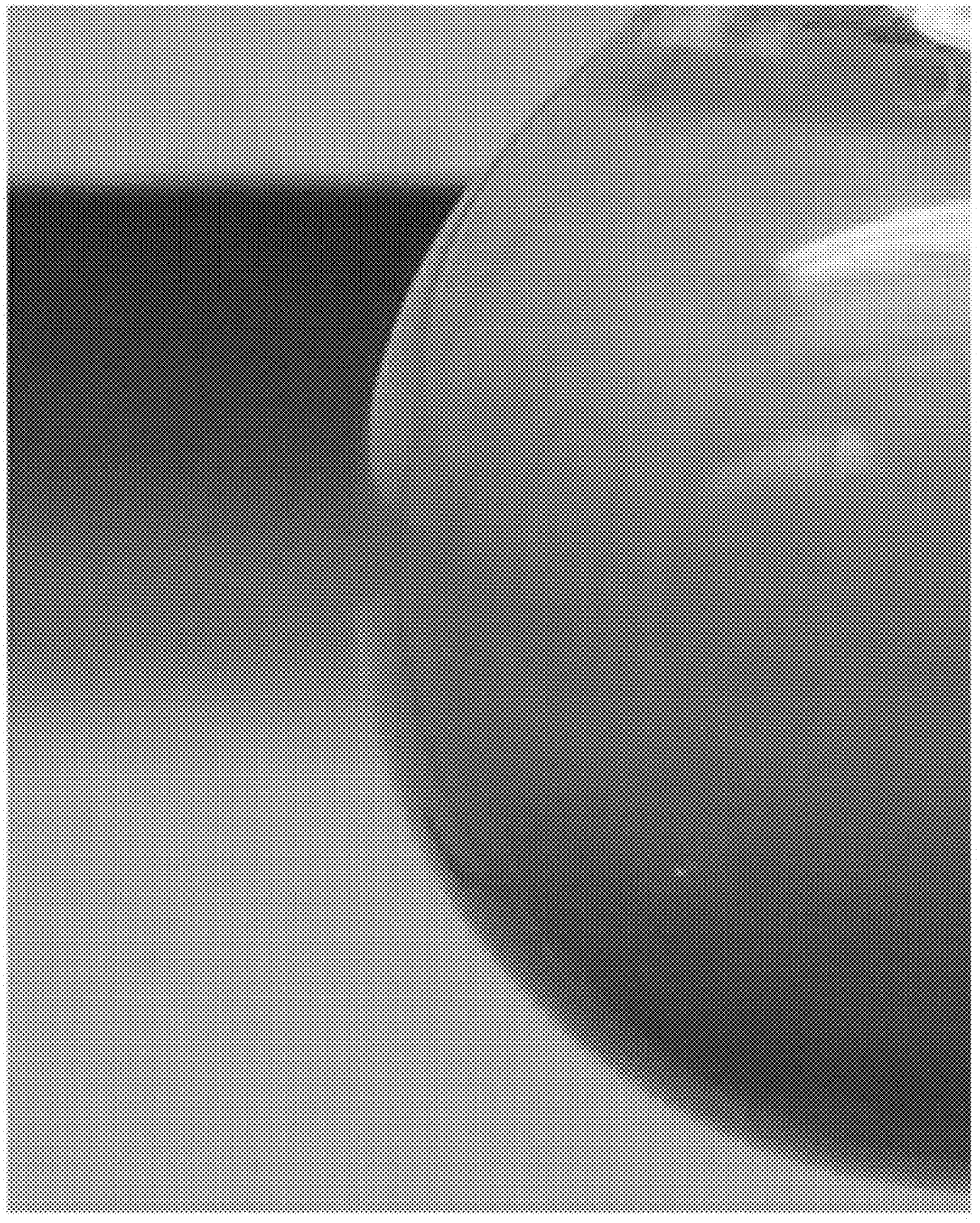

GC analysis of products after distillation of residual methanol, as well as ethanolamine, showed that the major products at the end of reaction were FAEA with small amounts of other impurities (FIG. 6 and FIG. 7). GC-MS analysis of the crude FAEA indicated that some of the remaining impurities may be monosaccharide derivatives (from the starch portion of the algae). Other possible impurities could be product isomers from acyl rearrangement and their derivatives. When decoloration was not performed after the isolation of FAME, the typical color of the isolated FAEA was dark brown, but was improved after charcoal treatment and filtration (FIG. 8A-FIG. 8B).

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

Materials and Methods

Equipment $^1$H NMR analyses were performed using Varian VXRS 400 4 (400 MHz) or Brucker Avance 600 (600 MHz) NMR spectrometers at ambient temperatures. Mass spectrometric analyses were performed using Hewlett-Packard Esquire Ion Trap LC-MS (electrospray) spectrometer. GC analyses were performed using HP 5890 series II chromatograph equipped with an auto injector HP 7672A (Hewlett Packard, Palo Alto, Calif., USA) and an FID detector. A Rtx-Biodiesel TG (fused silica) or an MXT Biodiesel TG (Siltek-treated stainless steel) capillary column (Restek, Bellefonte, Pa.) was used for the GC. The following method was used for all the GC analyses for this study: Oven temperature: 60° C.→370° C. (10° C./min; 6 min hold at 370° C.; total time 37 min). Injector temp: 250° C.; Detector temp: 370° C. Injection vol:

1 μL; Split mode: 40:3. Dry $N_2$ was used as a carrier gas with a column flow rate of 15 mL/min. Calibration curves were prepared for C14:0, C15:0, C16:0 and C22:6 fatty acid methyl esters and TMS derivatives of fatty acid ethanolamides for quantification ($r^2$>0.99).

Chemicals

Most reagents were purchased from commercial suppliers and used without further purification. Thin layer chromatography (TLC) was carried out on glass backed silica plates, purchased from Sorbent Technology. The plates were visualized under UV (254 nm) light, or by staining with either potassium permanganate or phosphomolybdic acid reagents and gentle heating. Silica gel column chromatography was carried out using 20-60 micron dry silica purchased from Sorbent Technology.

Microalgae Biomass

The microalgae strain *Schizochitrium limacinum* SR21 or *Chlorella Vulgaris* were used in these examples. The microalgal cultures were heterotrophically grown, harvested, and freeze-dried elsewhere. This microalgal strain is believed to have a high growth rate and lipid content and is thus well-suited as a model substrate for the present disclosure.

Analysis of Lipid Content and Composition

The method is based on an in situ transesterification procedure for quantification of FAME content of microalgal biomass. 20-30 mg of freeze-dried biomass was heated with 0.5 mL of acidified methanol solution (containing 5% (v/v) $H_2SO_4$) in a sealed crimp-top GC vial at 90° C. for 2 h using an oil bath (containing silicone oil) to convert algal lipids to FAMEs. After the incubation period was complete, the GC vial was removed from the oil bath and cooled to room temperature. The contents of the GC vial were then carefully transferred to an 8 mL screw-cap vial containing 4 mL hexane to extract the FAMEs from the acidified methanol reaction mixture. The GC vial was rinsed with an additional 1 mL hexane to remove any residual solids and also transferred to the 8-mL vial. Extraction of FAME into hexane was performed by heating the screw-cap vials at 90° C. for 15 min. After cooling, the vials were weighed and evaporation losses, if any, were compensated by addition of fresh hexane (usually 1-2 drops). Finally, an aliquot from the hexane layer was analyzed using GC, and FAME concentrations were quantified with calibration curves of reference standards. The lipid content of microalgae biomass used in this example was determined to be 290-330 mg/g biomass of lipid.

Fatty Acid Ethanolamide Synthesis and Recovery by In Situ Amidation Using Microalgae Strain *Schizochitrium limacinum*

Figure 10:
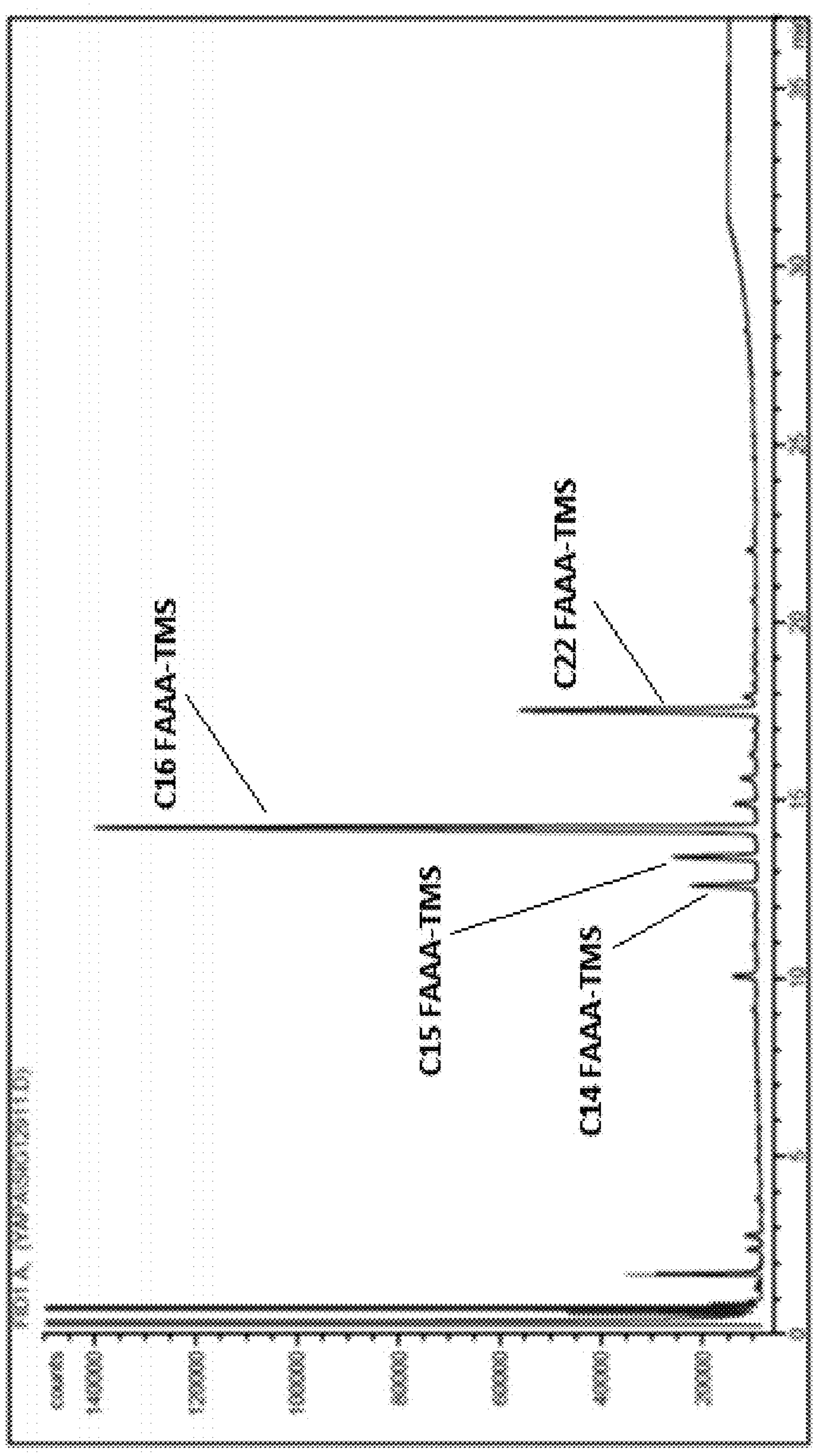
FIG. 10: GC chromatogram of TMS derivatives of FAEA extracted with EtOAc from microalgae strain *Schizochitrium limacinum.*

Freeze-dried microalgae biomass (*Schizochitrium limacinum,* 0.1 g) and ethanolamine (0.5 mL) were added to a 1.5 mL crimp-top GC vial. The vial was sealed and heated at 120° C. in an oil bath for 1.5 h with continuous stirring at 300 rpm. After the reaction period, the vial was cooled to room temperature and the contents were carefully transferred to an 8 mL glass centrifuge tube by first diluting with 1 mL of EtOAc and subsequently with three additional rinses with 1 mL EtOAc and 2 mL water (1 mL×3). After transfer, the 8 mL centrifuge tube contained 2 mL water and 2 mL EtOAc in addition to the reaction mixture. EtOAc formed a separate phase from the reaction mixture and allowed selective extraction of the FAEA. 0.1 g of NaCl was also added to the two-phase mixture to prevent emulsion formation and to minimize the partitioning of glycerol into the ethyl acetate phase. The contents of the centrifuge tube were shaken vigorously to facilitate rapid transfer of FAEA to the EtOAc phase and allowed to settle back into two phases. The EtOAc layer was recovered and transferred to a round bottom flask. The aqueous phase was contacted two more times with fresh EtOAc (2 mL×2) to extract any FAEA not recovered during the initial extraction. Pooled EtOAc fractions from the three extraction stages were dried using a rotary evaporator. The solid crude FAEA remaining in the flask (FIG. 9) was then dissolved in a mixture of bis (trimethylsilyl)amine and pyridine (1 mL each) along with catalytic amounts of trifluoroacetic acid (20 μL) for silation and quantification (see the subsection: Derivation method of FAAA for GC analysis). A GC chromatogram of the silylated crude FAAA is shown in FIG. 10.

Fatty Acid Ethanolamide Synthesis by Concurrent In Situ Transesterification and Amidation Using the Microalgae Strain *Schizochitrium limacinum*

This method was analogous to the previous method for in situ amidation but the reaction was carried out with a mixture of methanol and ethanolamine instead of ethanolamine alone. The following two mixture compositions were used in these reactions—(1) 0.1 mL methanol+0.4 mL ethanolamine and (2) 0.25 mL methanol+0.4 mL ethanolamine.

Fatty Acid Ethanolamide Synthesis by In Situ Transesterification Followed by Amidation Using the Microalgae Strain *Schizochitrium limacinum*

Freeze-dried microalgae biomass (*Schizochitrium limacinum,* 0.1 g) and Amberlyst 15 (40% g/g-biomass) were mixed with methanol (0.5 mL) in 1.5 mL crimp-top GC vial, sealed and heated at 90° C. for 6 h in an oil bath with continuous stirring at 300 rpm. After reaction was complete, the vials were removed, cooled to room temperature and centrifuged at 4000 rpm for 10 min. Two well-separated liquid phases were obtained. The upper FAME layer was recovered using a gas-tight syringe. Thereafter, 1 mL hexane was added into the vial to extract the remaining dissolved FAMEs from the lower phase; the hexane phase was subsequently recovered and combined with the previously recovered upper layer. Hexane was evaporated from the pooled liquid samples and the residual liquid was placed back in a 1.5 mL crimp-top GC vial, and ethanolamine (0.1 mL) and NaOMe (5% w/w) were charged. This mixture was incubated at reaction temperature (90° C. or 120° C.) for 1-15 h. After desired incubation periods, the vials were cooled to room temperature, and a portion of the crude mixture (40-80 mg) was recovered and silylated (see the sub-section: Derivatization method of FAAA for GC analysis) and subjected to GC analysis for quantification against the reference standards.

Fatty Acid Diethanolamide Synthesis and Recovery by In Situ Amidation Using Microalgae Strain *Chlorella Vulgaris*

Dried microalgae biomass (*Chlorella Vulgaris,* 1.0 g) and diethanolamine (5.0 mL) were added to a 20 mL crimp-top glass tube equipped with a magnetic stir bar. The glass tube was sealed and heated at 120° C. in an oil bath for 2.0 h with continuous stirring at 600 rpm. After the reaction completion, the glass tube was cooled to room temperature and then water (5 mL) followed by NaCl (1.0 g) were charged. The mixture was then extracted with EtOAc (5 mL×3) and the combined EtOAc layer was washed with water (2 mL×3), and dried over $MgSO_4$ and charcoal. The solid was removed by filtering through a pad of celite, and the filtrate was concentrated under reduced pressure to obtain 280 mg of fatty acid diethanolamide.

Fatty Acid Diethanolamide Synthesis by In Situ Transesterification Followed by Amidation Using Microalgae Strain *Chlorella Vulgaris*

Dried microalgae biomass (*Chlorella Vulgaris,* 1.0 g) was treated with acidified methanol (5.0 mL containing 5% by volume of concentrated $H_2SO_4$) in a 20 mL crimp-top glass tube equipped with a magnetic stir bar. The glass tube was sealed and heated at 90° C. in an oil bath with continuous stirring at 600 rpm. After completion of transesterification (~2 hours), the reaction tube was cooled to room temperature and centrifuged at 4000 rpm for 10 min. The upper layer was separated using a gas-tight syringe. The crude lower phase was treated with hexane (5 mL×3) to extract the remaining FAMEs, and the organic phases were combined with the previously separated upper phase of FAMEs. The organic mixture was then treated with charcoal, passed through a pad of celite to remove charcoal, and hexane was removed under reduced pressure. The obtained crude product was mixed with bis(2-hydroxyethyl)amine (1.0 g) and sodium methoxide (15 mg). This mixture was heated at 120° C. until the completion of the reaction (2.5 h) and cooled to room temperature. The reaction mixture was dissolved in dichloromethane (15 mL) and washed with water (5 mL×3). The dichloromethane layer was dried with anhydrous $MgSO_4$, filtered through a pad of celite, and the solvent removed under reduced pressure to obtain 293 mg of the product as a light brown waxy solid.

Fatty Acid Diisopropanolamide Synthesis and Recovery by In Situ Amidation Using Microalgae Strain *Chlorella Vulgaris*

Fatty acid diisoproanolamide was prepared following the procedure described above for the synthesis of diethanolamide by in situ amidation. The product was obtained from 1 g of dried biomass as a light brown waxy solid (307 mg).

Fatty Acid Diisopropanolamide Synthesis by In Situ Transesterification Followed by Amidation Using Microalgae Strain *Chlorella Vulgaris*

Fatty acid diisopropanolamide was prepared following the procedure described above for the synthesis of diethanolamide by in situ transesterification followed by amidation method. The product was obtained from 1 g of dried biomass as a light brown waxy solid (294 mg).

General Synthesis Procedure of Alkanolamide Reference Standards

The substrate (free fatty acid) was placed in a three-necked flask and dissolved in methanol (12 mL/g). Acetyl chloride (1.2 equiv.) catalyst was added and the mixture was heated to reflux under nitrogen atmosphere for several hours. After completion of methyl ester formation, a part of the solvent (methanol) was removed under reduced pressure, the reaction mixture was extracted with diethylether, and the diethyether layer was washed three times with 5% $NaHCO_3$ and dried over anhydrous $MgSO_4$. Dried diethylether layer was filtered and crude methyl ester was recovered by removing diethylether under reduced pressure. The methyl ester was carried to the next step without further purification. The crude material was treated with alkanolamine (~6 equiv.) for several hours at ambient temperature and was recrystallized from methanol (except for $C_{22}$ FAAA synthesis where purification was achieved by column chromatography using 3:7 acetone:hexane mixture as the eluent) to obtain the pure alkanolamides. The identity and purity of the isolated products were confirmed by 1H-NMR, mass spectrometry, and GC (for ethanolamides). NMR spectra are shown in FIGS. 12A-12B, 13A-13B, 14A-14B, 15A-15B, 19A-19B, 20A-20B, 21A-21B, 22A-22B, 23, and 24.

N-(2-hydroxyethyl)tetradecanamide

Yield 40.1%, white crystals, $^1$H-NMR (600 MHz, $CDCl—_3$) δ (ppm); 5.97 (s, 1H, —NH—), 3.71-3.73 (m, 2H, —$CH_2$OH), 3.41-3.43 (m, 2H, —$CH_2$NH—), 2.20 (t, J=7.5 Hz, 2H, —$CH_2$CO—), 1.60-1.65 (m, 2H, —$CH—_2$—), 1.25-1.30 (m, 20H, —$(CH_2)_{10}$—), 0.87 (t, J=6.96 Hz, —$CH_3$). $^{13}$C NMR (600 MHz, $CDCl_3$) δ (ppm): 174.8, 62.8, 42.6, 36.8, 32.1, 29.8, 29.6, 29.5, 29.4, 25.9, 22.8, 14.3. NMR spectral data matched that of the literature.

N-(2-hydroxyethyl)pentadecanamide

Yield 76%, white crystals, $^1$H-NMR (600 MHz, DMSO) δ (ppm): 7.75 (s, 1H, —NH—), 4.63 (s, 1H, —OH), 3.36 (m, 2H, —$CH_2$OH), 3.07-3.10 (m, 2H, —N$HCH_2$—), 2.02-2.05 (t, J=7.32 Hz, 2H, —CO$CH_2$—), 1.44-1.47 (m, 2H, —$CH_2$—), 1.23 (m, 22H, —$CH_2$), 0.85 (t, J=6.6 Hz, 3H, —$CH_3$). $^{13}$C NMR (600 MHz, DMSO) δ (ppm): 172.2, 60.0, 41.1, 35.4, 31.3, 29.1, 29.0, 28.8, 28.7, 25.3, 22.1, 14.0. NMR spectral data match that of the literature.

N-(2-hydroxyethyl)palmitamide

Yield 90.5%, white crystals, $^1$H-NMR (600 MHz, $CDCl_3$) δ (ppm): 5.69 (s, 1H, —NH—), 3.73 (t, J=4.9 Hz, 2H, —$CH_2$OH), 3.43 (m, 2H, —$CH_2$NH—), 2.20 (t, J=7.6 Hz, 2H, —CO$CH_2$—), 1.60-1.64 (m, 2H, —$CH_2$—), 1.23 (m, 24H, —$CH_2$—), 0.88 (t, J=7.0 Hz, 3H, —$CH_3$), $^{13}$C NMR (600 MHz, $CDCl_3$) δ (ppm): 173.7, 132.2, 129.5, 128.7. 128.4. 128.3, 128.2, 128.1, 127.2, 51.7, 34.2, 25.8, 25.7, 22.94, 20.7. NMR spectral data matches with that of the literature.

(4Z,7Z,10Z,13Z,16Z,19Z)—N-(2-hydroxyethyl)docosa-4,7,10,13,16,19-hexaenamide.

Yield 35.3%, colorless oil, $^1$H-NMR (600 MHz, $CD_3OD$) δ (ppm): 5.28-5.41 (m, 12H, —CH═CH—), 3.58 (t, J=5.88 Hz, 2H, —$CH_2$OH), 3.28 (t, J=5.52 Hz, 2H, —N$HCH_2$—), 2.82-2.89 (m, 10H, —$CH_2$—), 2.37-2.40 (m, 2H, —$CH_2$—), 2.24 (t, J=7.82 Hz, 2H, —CO$CH_2$—), 2.06-2.11 (m, 2H, —$CH_2$—), 0.97 (t, J=7.56 Hz, 3H, —$CH_3$); $^{13}$C NMR (600 MHz, $CDCl_3$) δ (ppm): 173.8, 132.2, 129.6, 128.7, 128.5, 128.4, 128.2, 128.1, 128.0, 127.1, 62.7, 42.6, 36.5, 25.8, 25.7, 23.5, 20.7, 14.4. NMR spectral data match that of the literature.

N-bis(2-hydroxyethyl)palmitnamide

Yield 73.2%, white solid, $^1$H-NMR (600 MHz, $CDCl_3$) δ (ppm): 3.87 (t, J=4.8 Hz, 2H, —$CH_2$OH), 3.79 (t, J=4.8 Hz, 2H, —$CH_2$OH), 3.57 (t, J=4.8 Hz, 2H, —N$CH_2$—), 3.51 (t, J=4.8 Hz, 2H, —N$CH_2$—), 2.39 (t, J=7.8, 2H, —$CH_2$CO—), 1.61-1.67 (m, 2H, —$CH_2CH_2$CO—), 1.25-1.30 (m, 24H), 0.88 (t, J=7.2 Hz, 3H, $CH_3$); $^{13}$C NMR (600 MHz, $CDCl_3$) δ (ppm): 175.78, 61.69, 60.88, 52.23, 50.58, 33.66, 31.94, 29.71, 29.70, 29.67, 29.57, 29.51, 29.48, 29.38, 25.31, 22.71, 14.15.

N-bis(2-hydroxyethyl)oleamide

Yield 72.7%, colorless oil, $^1$H-NMR (600 MHz, $CDCl_3$) δ (ppm): 5.33-5.35 (m, 2H, —CH═CH—), 3.84 (t, J=4.8 Hz, 2H, —$CH_2$OH), 3.77 (t, J=4.8 Hz, 2H, —$CH_2$OH), 3.56 (t, J=4.8 Hz, 2H, —N$CH_2$—), 3.49 (t, J=4.8 Hz, 2H, —N$CH_2$—), 2.39 (t, J=7.8, 2H, —$CH_2$CO—), 2.00 (m, 4H, —$CH_2$—CH═CH—$CH_2$—), 1.62-1.64 (m, 2H, $CH_2CH_2$CO—), 1.24-1.31 (m, 20H), 0.88 (t, J=7.2 Hz, 3H, $CH_3$); $^{13}$C NMR (600 MHz, $CDCl_3$) δ (ppm): 175.72, 130.08, 129.83, 61.34, 60.81, 33.74, 32.00, 29.86, 29.84, 29.63, 29.53, 29.51, 29.42, 29.31, 27.31, 27.30, 25.40, 22.78, 14.22.

N-bis(2-hydroxypropyl)palmitamide

Yield 69.2%, white solid, $^1$H-NMR (600 MHz, $CDCl_3$) δ (ppm): 4.13-4.22 (m, 1H, —CHOH—), 3.99-4.03 (m, 1H, —CHOH—), 3.12-3.49 (m, 4H, two —N$CH_2$—), 2.29-2.44 (m, 2H, —$CH_2$CO—), 1.59-1.65 (m, 2H, $CH_2CH_2$CO—), 1.17-1.31 (m, 30H), 0.88 (t, J=7.2 Hz, 3H, —$CH_2CH_3$); $^{13}$C NMR (600 MHz, $CDCl_3$) δ (ppm): 175.98, 67.60, 66.97, 66.30, 65.07, 58.64, 57.38, 56.96, 55.52, 33.74, 33.66, 31.94, 29.71, 29.67, 29.56, 29.55, 29.51, 29.47, 29.38, 25.29, 22.71, 21.59, 21.47, 20.65, 20.33, 14.15. NMR signals for amide group and —$CH_2CO$— are splitted abnormally.

N-bis(2-hydroxypropyl)oleamide.

Yield 74.3%, colorless oil, $^1H$-NMR (600 MHz, $CDCl_3$) δ (ppm): 5.35-5.37 (m, 2H, —CH═CH—), 4.16-4.26 (m, 1H, —CHOH—), 4.01-4.04 (m, 1H, —CHOH—), 3.14-3.48 (m, 4H, two —$NCH_2$—), 2.32-2.46 (m, 2H, —$CH_2CO$—), 2.00-2.04 (m, 4H, —$CH_2$—CH═CH—$CH_2$—), 1.62-1.66 (m, 2H, $CH_2CH_2CO$—), 1.19-1.33 (m, 30H), 0.90 (t, J=7.2 Hz, 3H, —$CH_2CH_3$); $^{13}C$ NMR (600 MHz, $CDCl_3$) δ (ppm): 175.98, 175.92, 129.99, 129.97, 129.80, 129.78, 67.74, 66.98, 66.41, 65.12, 58.55, 57.33, 56.82, 55.47, 33.70, 33.63, 31.91, 29.78, 29.75, 29.54, 29.42, 29.41, 29.33, 29.20, 29.19, 27.22, 27.21, 25.25, 22.70, 21.68, 21.54, 20.63, 20.34, 14.14. NMR signals for amide group and —$CH_2CO$— are splitted abnormally.

Scale Up of Alkanolamides Synthesis and Quality Upgrade 1 g of dried biomass and Amberlyst 15 (40% (w/w)) were dissolved in methanol (5.0 mL/g) in a 8 mL screw cap vial and heated at 90° C. in an oil bath with continuous stirring at 300 rpm. After completion of transesterification, the vial was cooled to room temperature and centrifuged at 4000 rpm for 10 min. The upper layer was separated using a gas-tight syringe. The crude lower phase was treated with hexane (10.0 mL/g of initial biomass weight) to extract the remaining FAMEs, and the resulting hexane phase was combined with the previously separated upper phase of FAMEs. Hexane was removed under reduced pressure and the crude liquid product was mixed with ethanolamine (1.0 mL/g of initial biomass weight). This mixture was heated for 3 hours at 120° C. and cooled to room temperature.

The reaction mixture (predominantly FAEAs) was distilled using Kügelrohr distillation apparatus under 30 mmHg vacuum at 70° C. The resulting crude FAEA was dissolved in minimal amount of methanol and treated with 10 w % activated charcoal and heated to 50° C. with stirring for 10 min. The mixture was filtered through a pad Cellite® under vacuum and the filtrate was concentrated to afford a light brown solid (FIGS. 8A-8B).

Derivatization Method of FAEA for GC Analysis

Figure 11A:
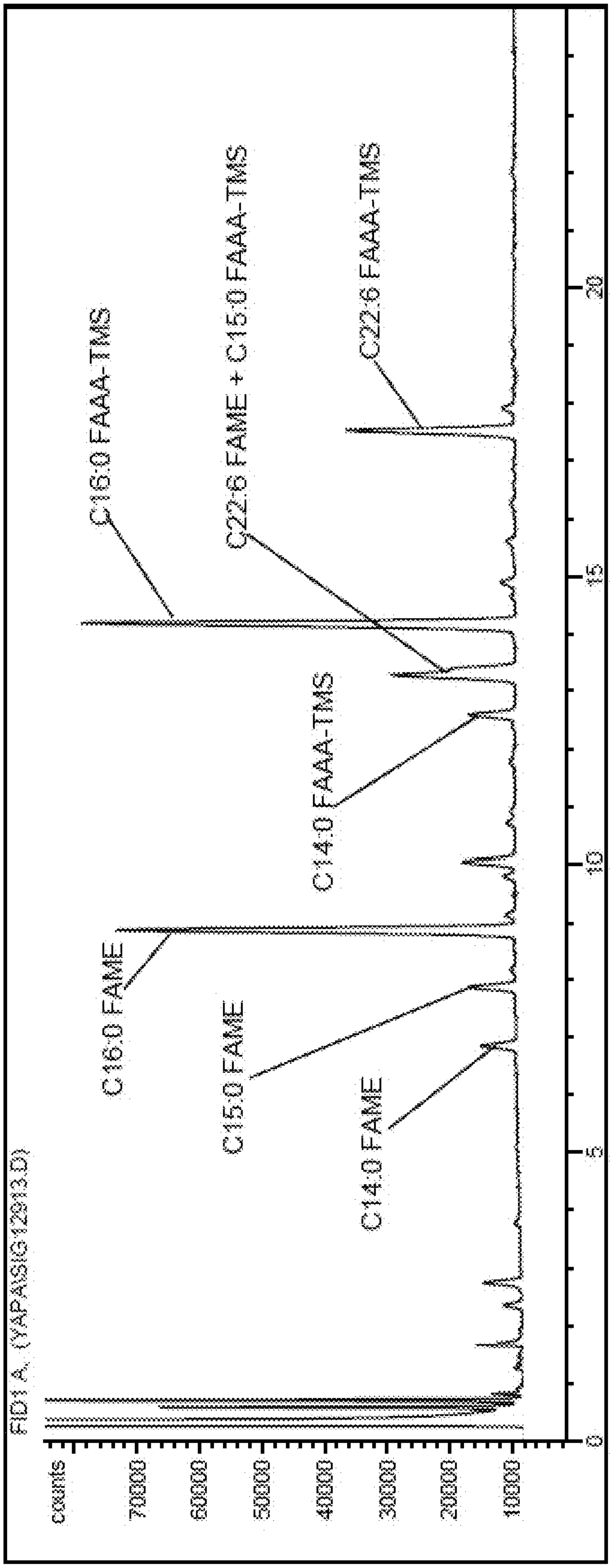
FIGS. 11A-11B: GC chromatogram of TMS derivatives of FAEA and FAMEs, extracted into EtOAc from microalgae strain *Schizochitrium limacinum*. The reaction medium contained a mixture of methanol and ethanolamine (total: 0.5 mL), in 4:1 proportion (FIG. 11A), and in 1:1 proportion (FIG. 11B).
Figure 11B:
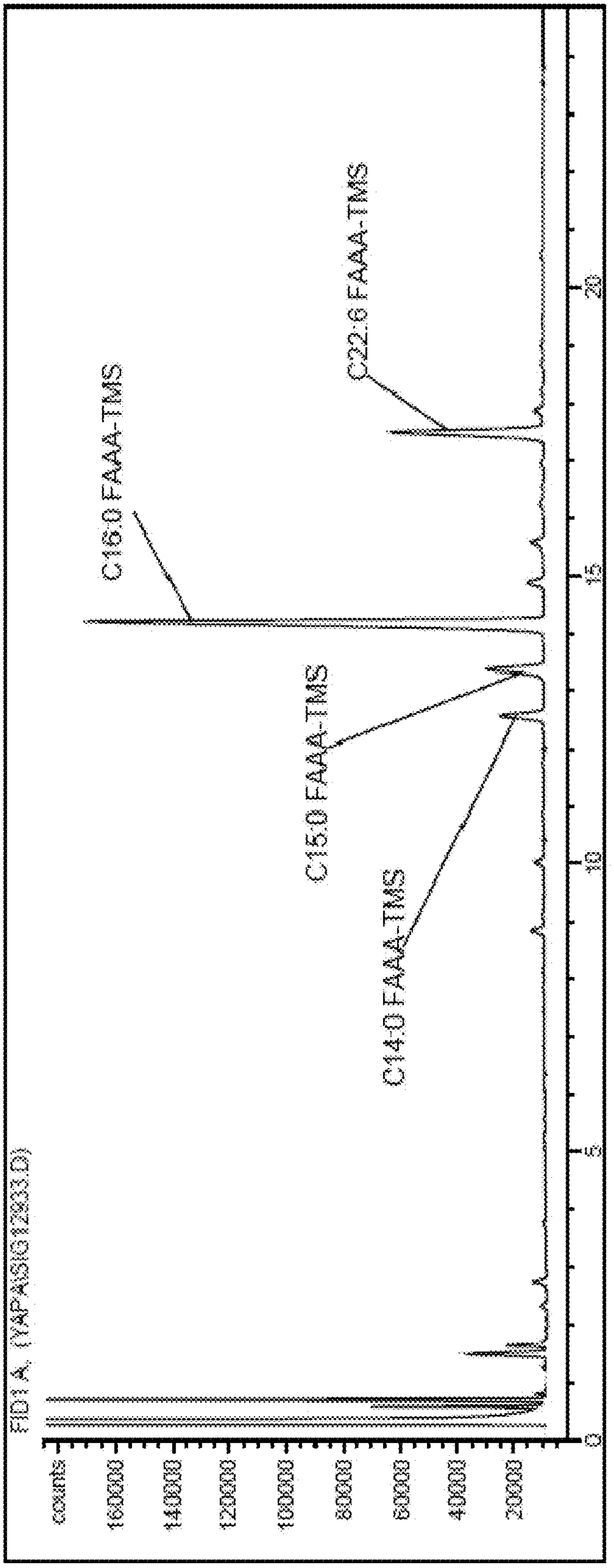
Figure 12A:
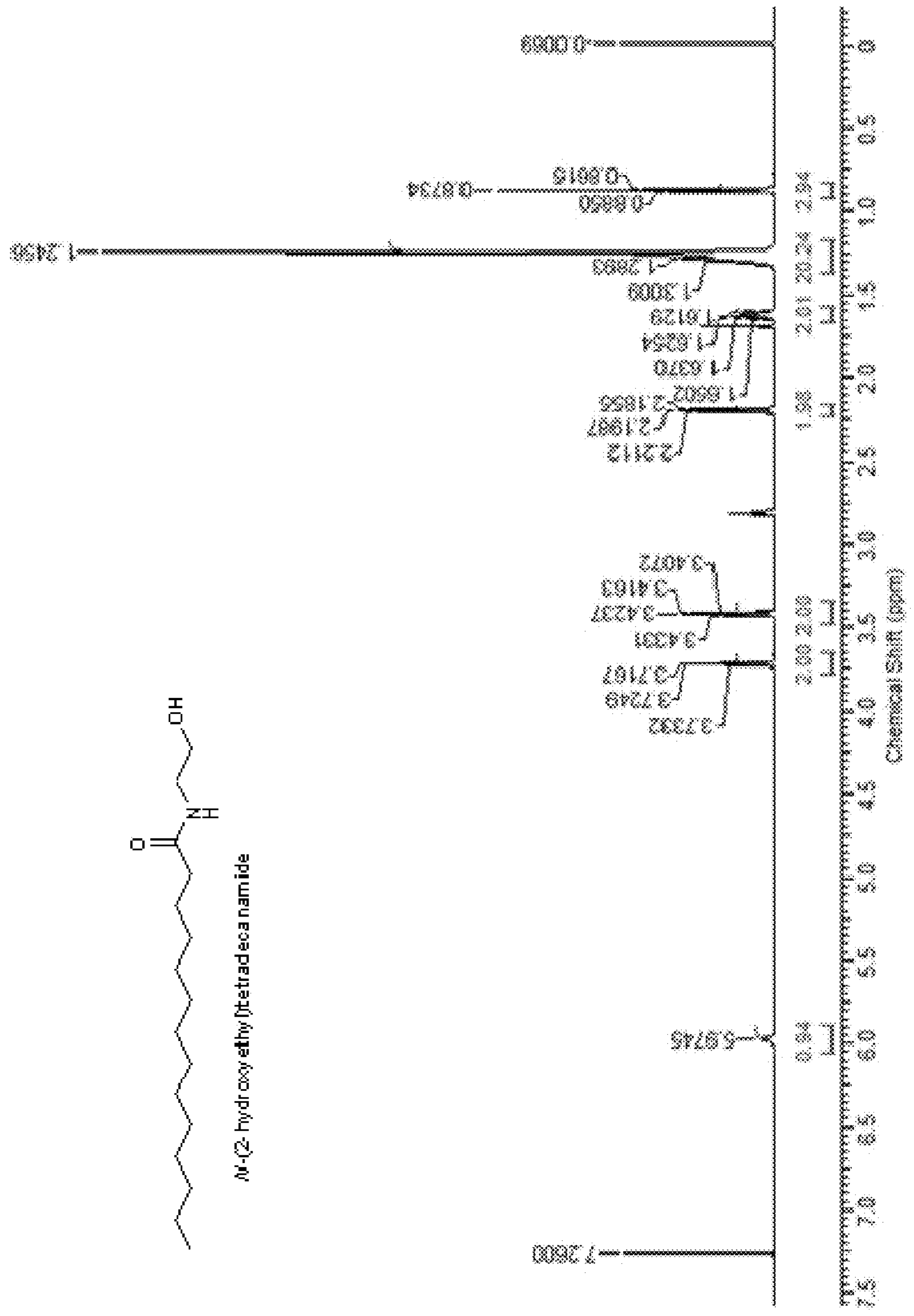
FIGS. 12A-12B: NMR spectra for N-(2-hydroxyethyl) tetradecanamide—a model FAEA.
Figure 12B:
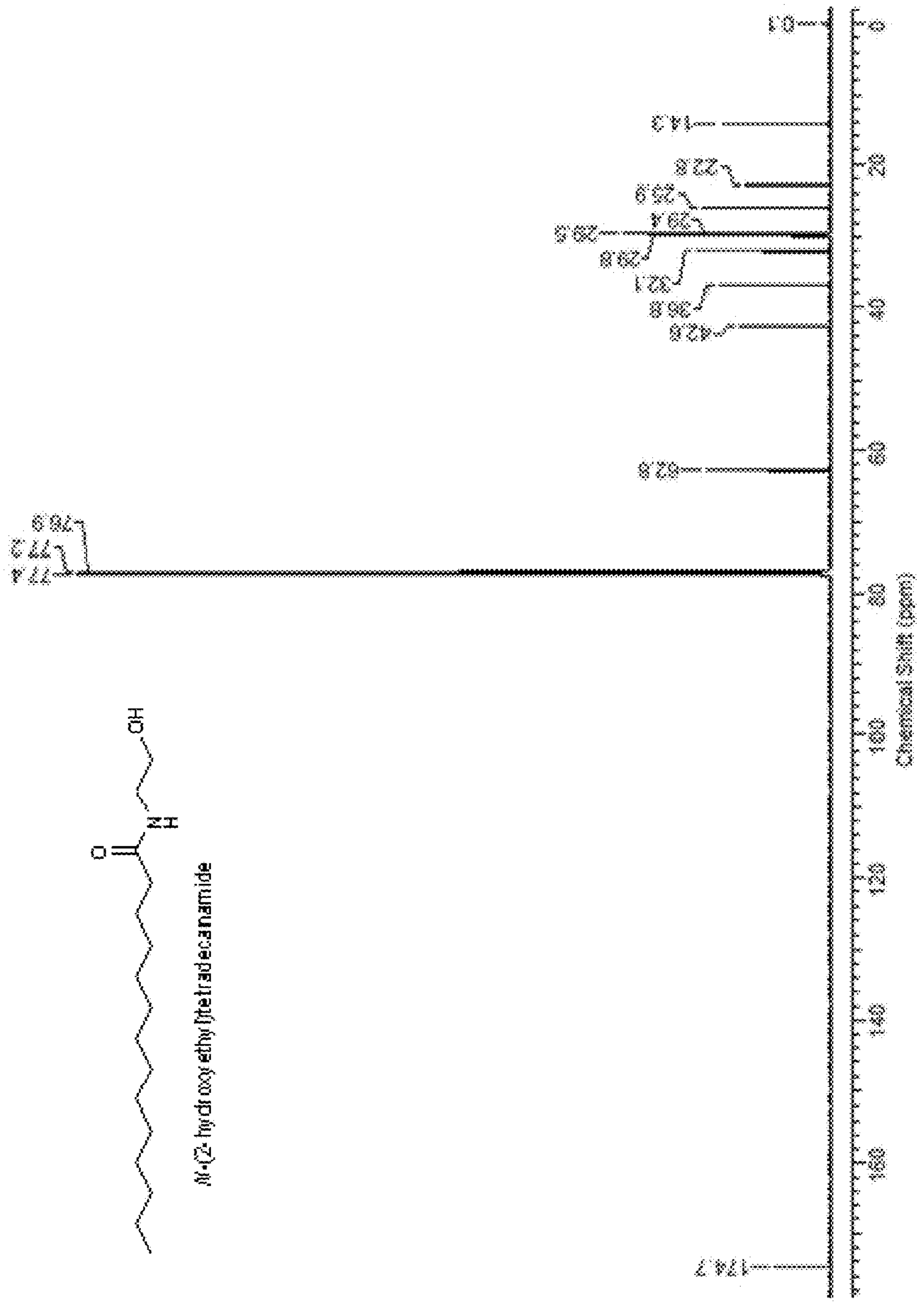
Figure 13A:
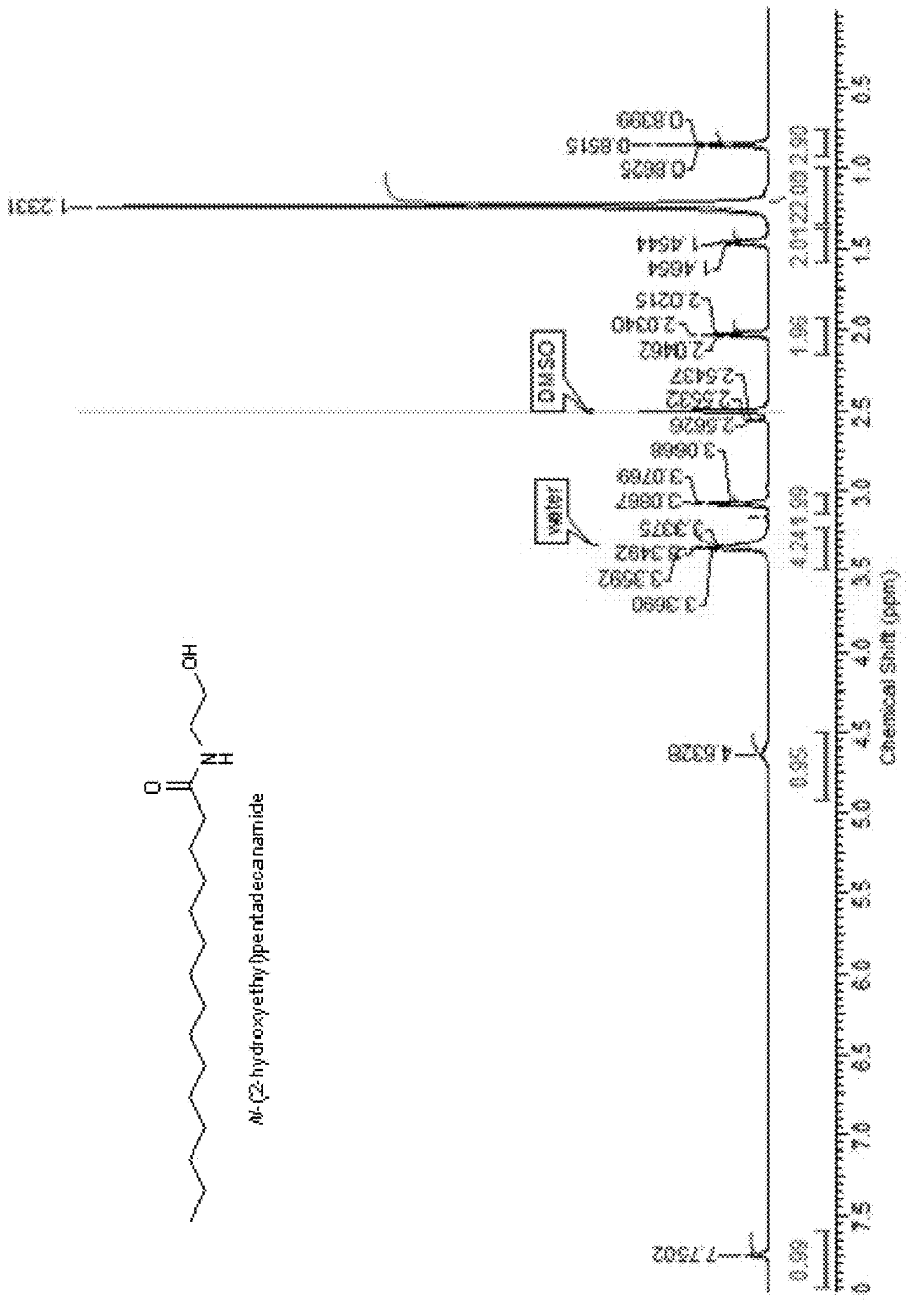
FIGS. 13A-13B: NMR spectra for N-(2-hydroxyethyl) pentadecanamide—a model FAEA.
Figure 13B:
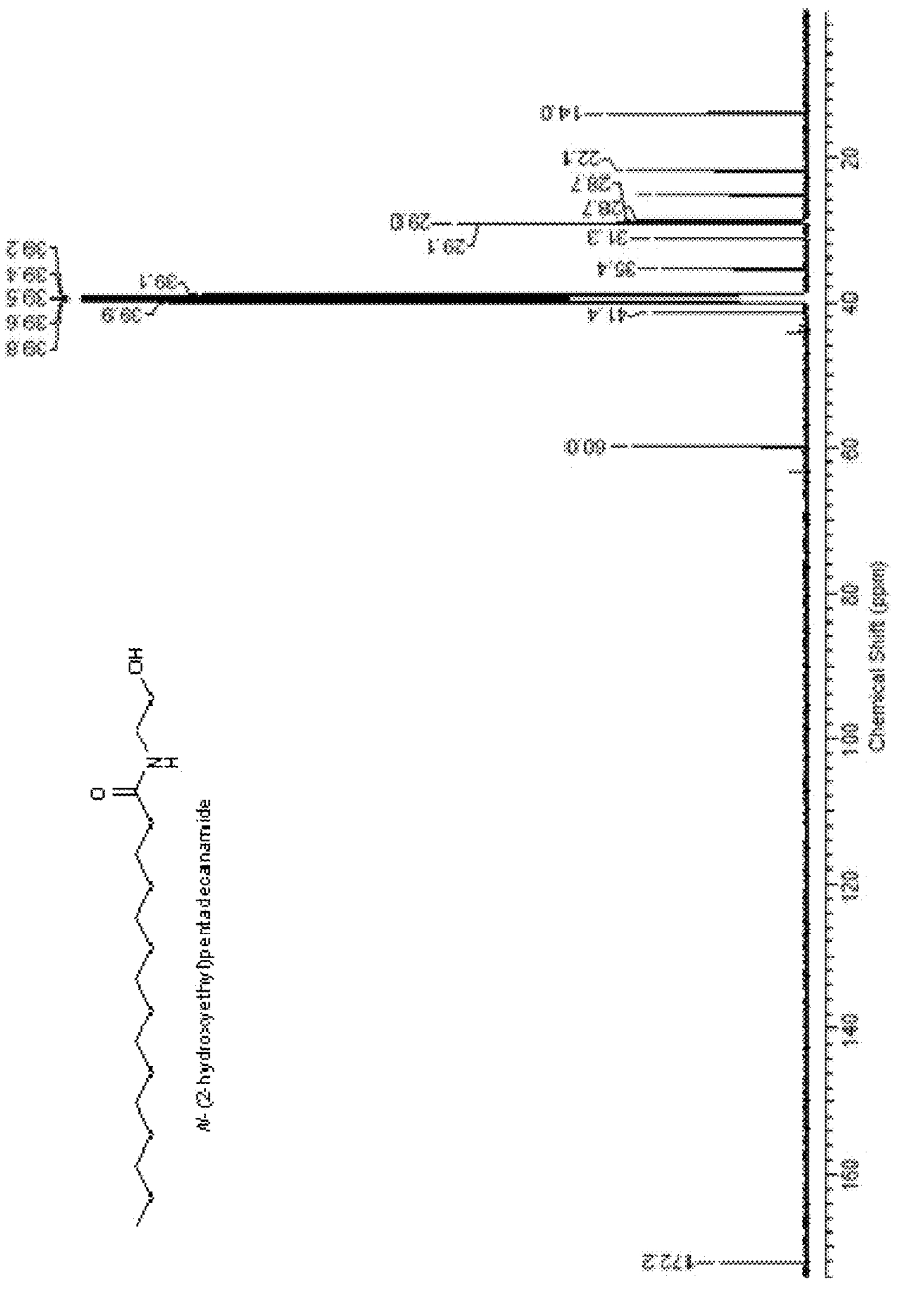
Figure 14A:
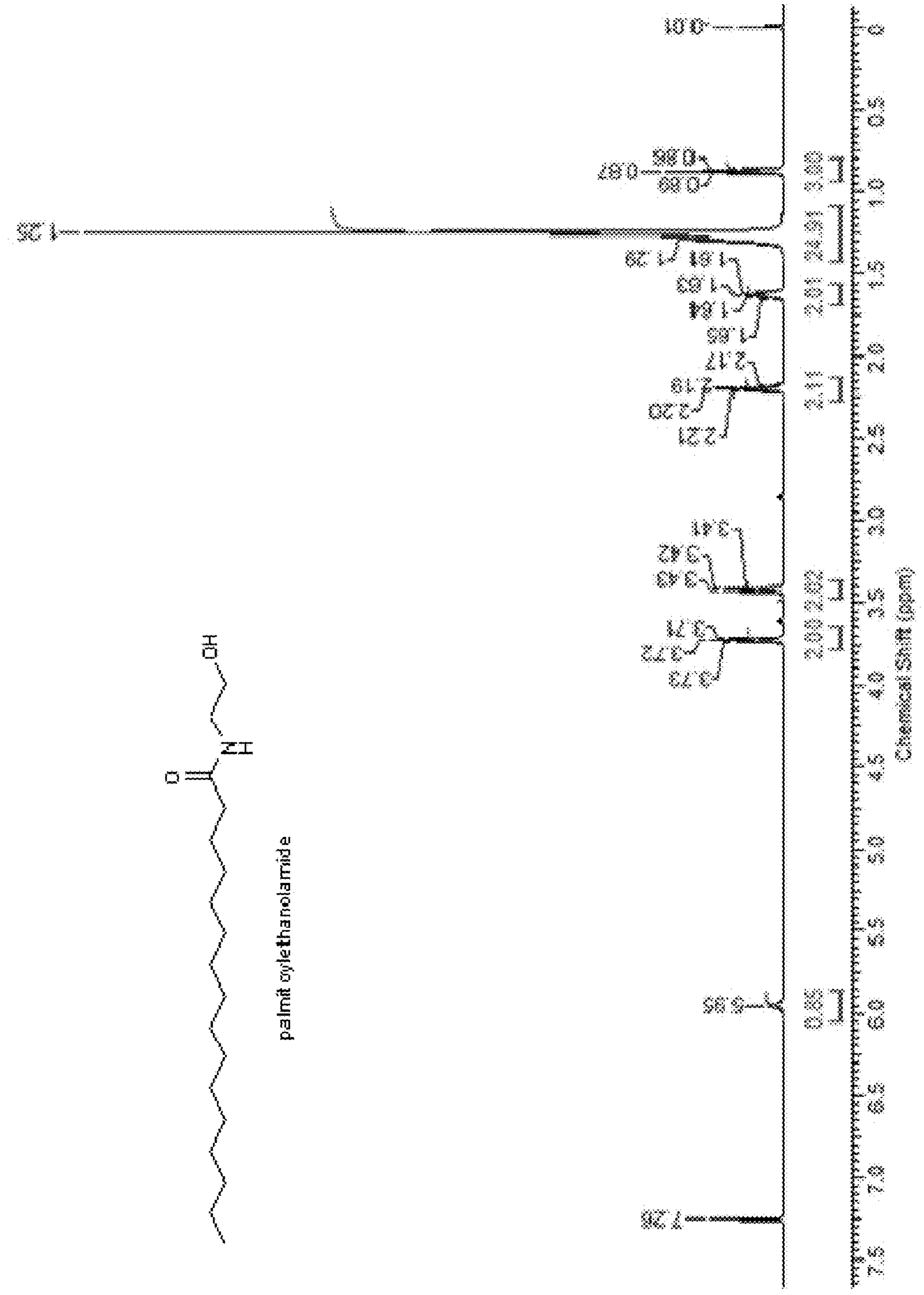
FIGS. 14A-14B: NMR spectra for N-(2-hydroxyethyl) palmitamide—a model FAEA.
Figure 14B:
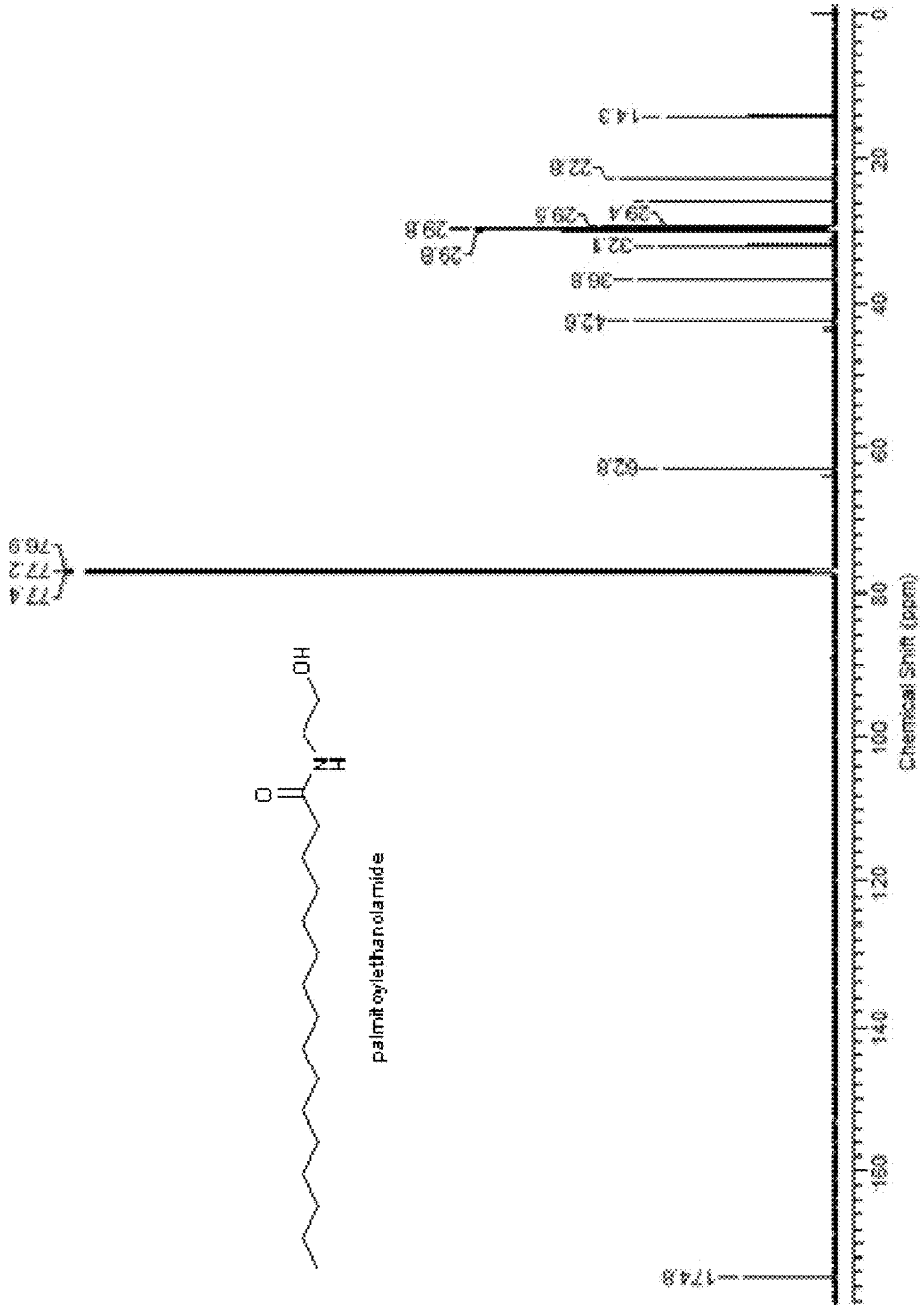
Figure 15A:
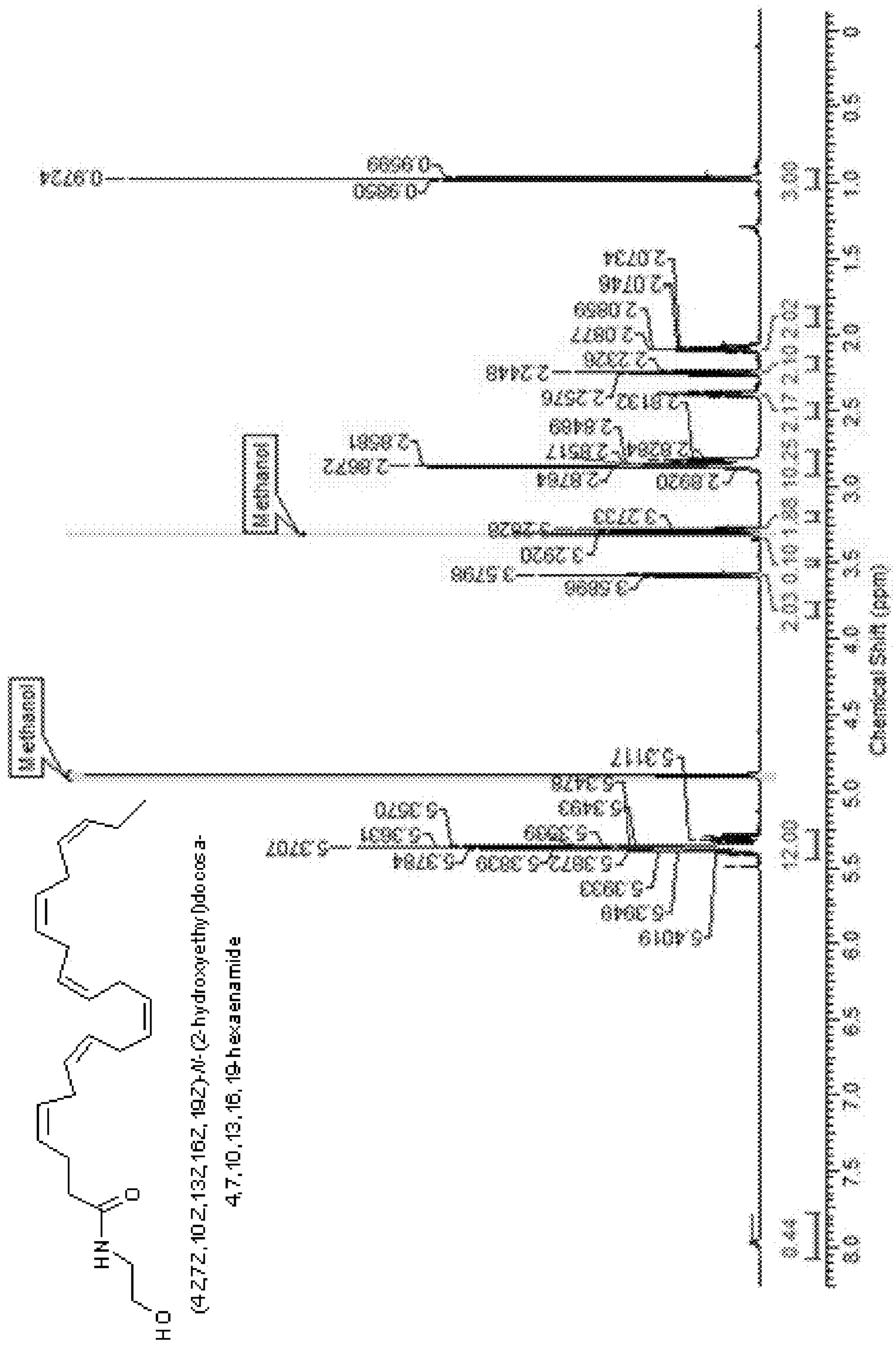
FIGS. 15A-15B: NMR spectra for (4Z,7Z,10Z,13Z,16Z, 19Z)—N-(2-hydroxyethyl)docosa-4,7,10,13,16,19-hexaenamide—a model FAEA.
Figure 15B:
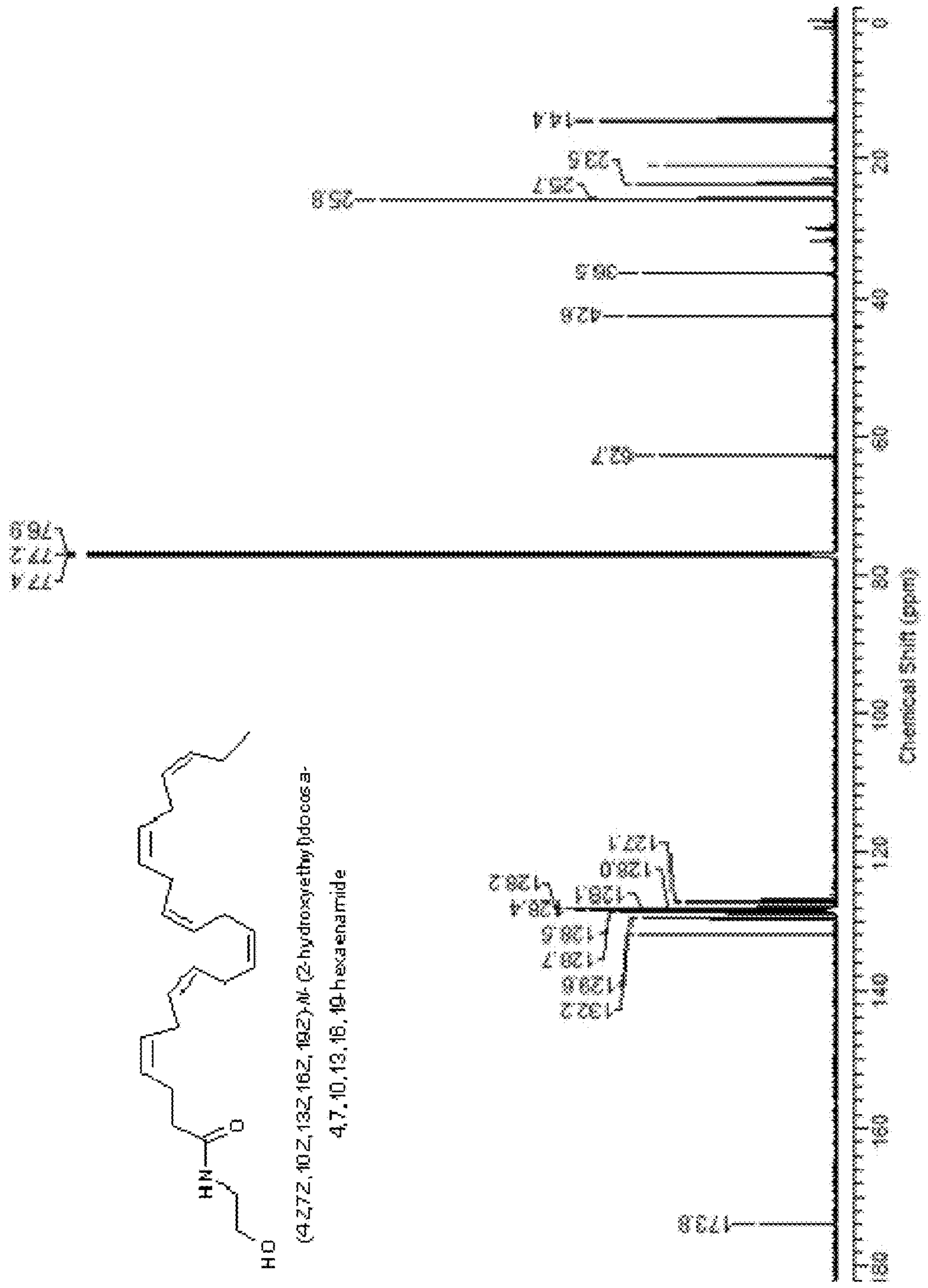
Figure 16A:
FIG. 16A: Photograph of the reaction mixture, when microalgae strain *Chlorella Vulgaris* and diethanolamine (DEA) was used, following the completion of the reaction scheme shown in FIG. 1A. Emulsion formation interfered with phase separation of FADEAs or FADIPAs from the reaction mixture; however, FAAAs can be selectively extracted into a solvent immiscible with the reaction mixture.
Figure 16B:
FIG. 16B: Photograph of the reaction mixture, when microalgae strain *Chlorella Vulgaris* was used, following the completion of the first-step of the two-step reaction scheme shown in FIG. 1C. Clear separation of FAMEs (upper phase) and methanol (lower phase) is seen at the end of the in situ transesterification step. The separated FAME layer is reacted in a second-step with diethanolamine or diisopropaneolamine to form FADEA or FADIPA, respectively.
Figure 17:
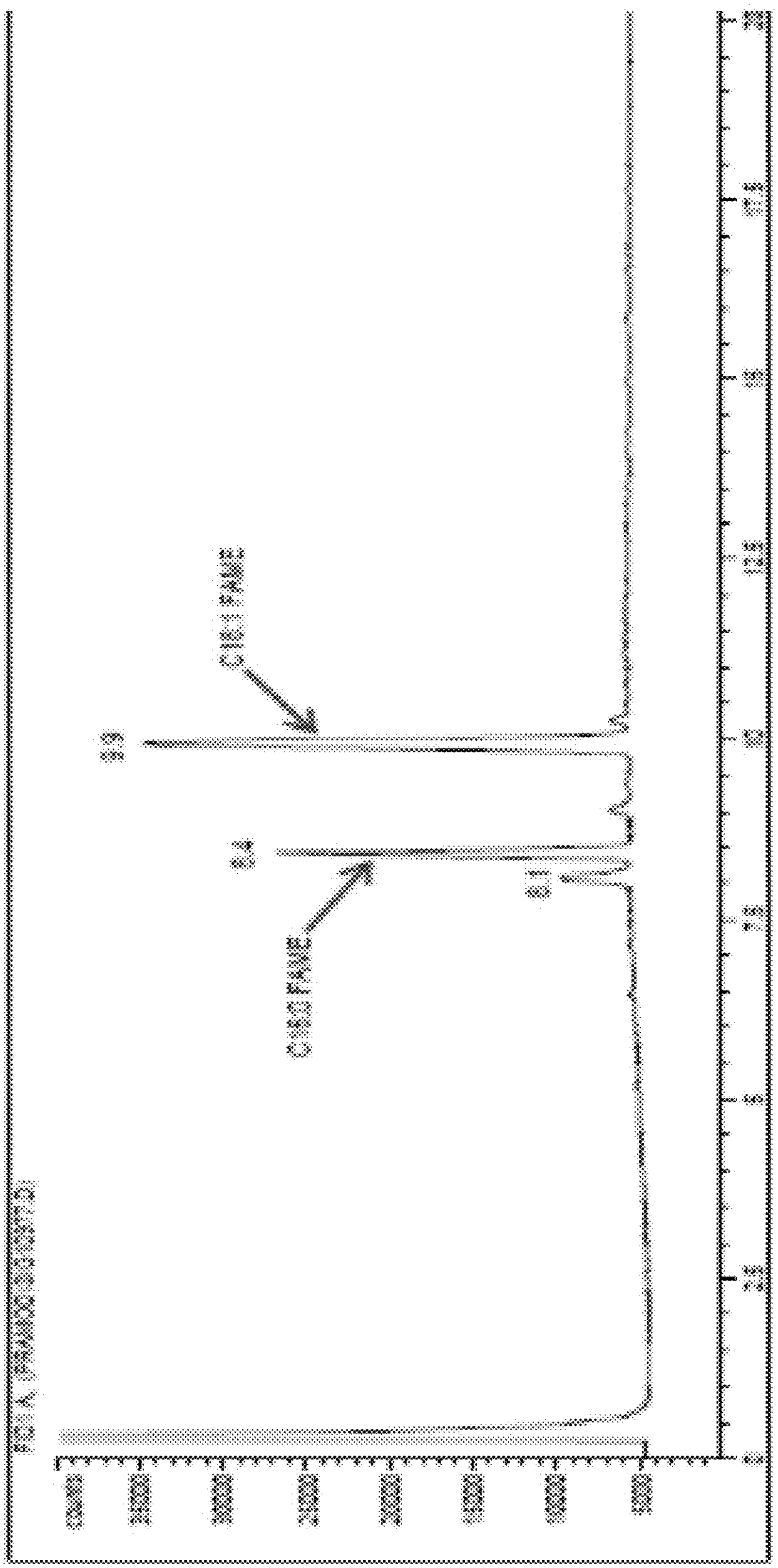
FIG. 17: GC chromatogram of FAMEs isolated from microalgae strain *Chlorella Vulgaris* after transesterification step (FIG. 1C, 3, procedure 3).
Figure 18A:
FIGS. 18A-18C: The typical color of the FAMEs isolated from microalgae strain *Chlorella Vulgaris* was dark brown (FIG. 18A), but was pale yellow after charcoal treatment (10% w/w-biomass) and filtration (FIGS. 18B and 18C).
Figure 18B:
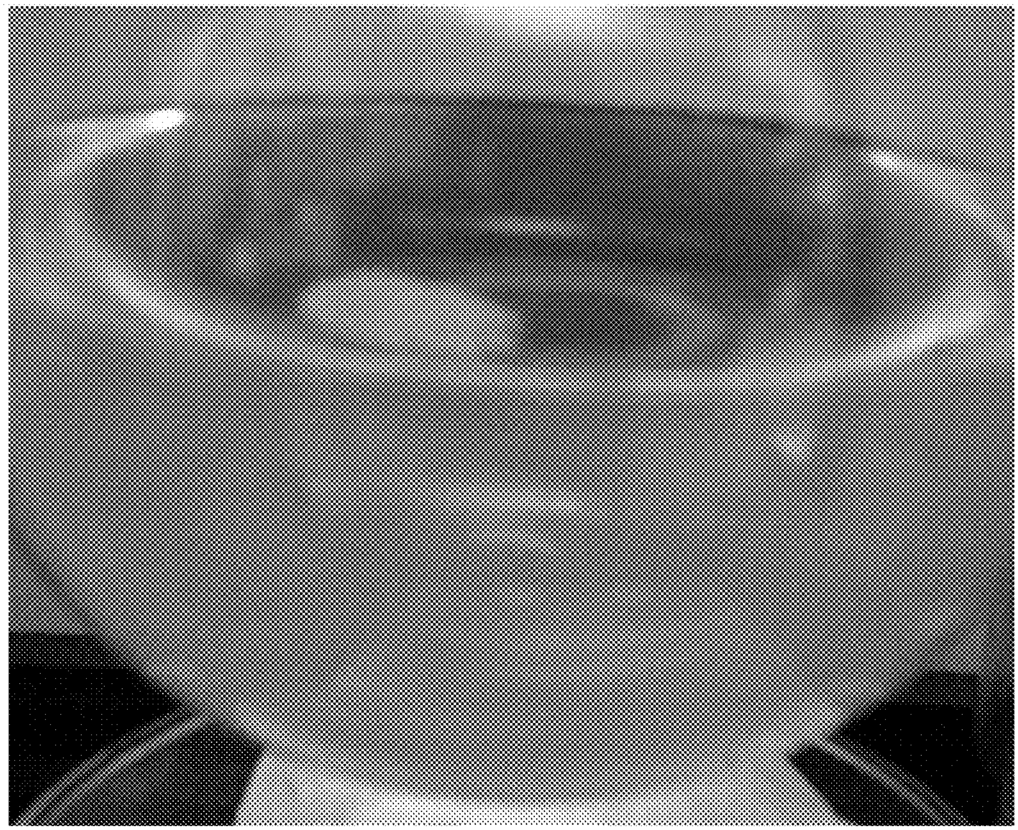
Figure 18C:
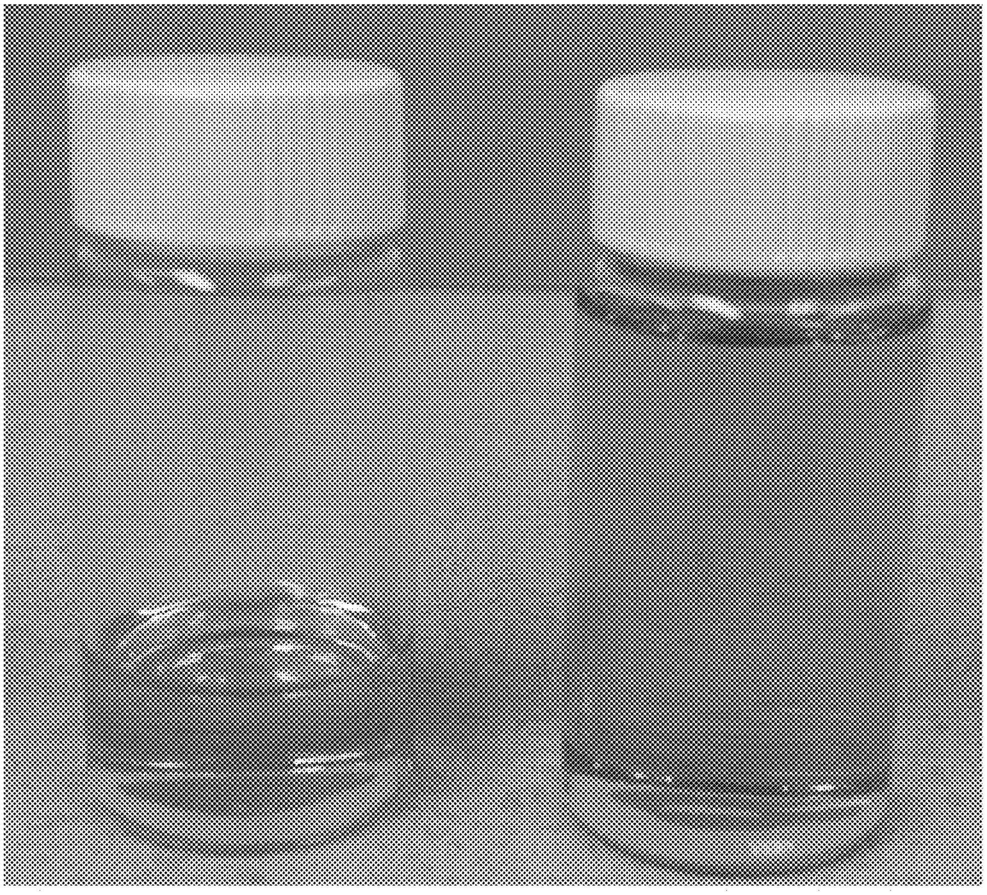

Since FAEA is known to rearrange to oxazoline under GC conditions, derivatization is required for its accurate quantification. This procedure is as follows: a mixture of bis (trimethylsilyl)amine (0.75 mL), pyridine (0.75 mL), and trifluoroacetic acid (20 μL) and a known mass of FAAA (40-80 mg) was heated at 70° C. for 30 min with a heating block with constant stirring at 500 rpm. The mixture was cooled to room temperature and diluted to 2 mL with hexane for GC analyses. (FIG. 10 and FIG. 11B.)

Large Scale Conversion of Algal Biomass into Fatty Acid Bis(2-Hydroxyethyl)Amide Derivative A mixture of 87.3 g of dried algae biomass (*Chlorella Vulgaris*) and acidified methanol (500 mL containing 5% by volume of concentrated sulfuric acid) was charged in a 1000 mL screw cap glass bottle containing a magnetic stir bar. The mixture was heated at 90° C. in an oil bath with continuous stirring at 600 rpm. After completion of transesterification (~2 hours), the reaction bottle was cooled to room temperature and centrifuged at 4000 rpm for 10 min. The upper layer was separated using a gas-tight syringe. The crude lower phase was extracted with hexane (300 mL×3), and the resulting organic phases were combined with the previously separated upper phase of FAMEs. The organic mixture was then treated with charcoal (3.5 g, ~4 wt % of dried biomass), and passed through a pad of celite, and hexane was removed under reduced pressure. The crude liquid product (26.23 g) thus obtained was mixed with bis(2-hydroxyethyl)amine (78.69 g) and sodium methoxide (1.32 g, 5 wt % of FAME). This mixture was heated at 120° C. until the completion of the reaction (2.5 h), and cooled to room temperature. Dichloromethane (150 mL) was added to the reaction mixture and the resultant solution was poured into a separatory funnel containing a mixture of 10% aq. HCl (300 mL) and dichloromethane (350 mL). The dichloromethane layer was further washed with water (300 mL×3), dried with anhydrous $MgSO_4$, filtered, and solvent was removed under reduced pressure to provide fatty acid bis(2-hydoxyethyl)amides (27.34 g) as a light brown waxy solid. The identity of the products was confirmed by comparing $^1H$ NMR of the product with that of standard amides [N-bis(2-hydroxyethyl) palmitanamide and N-bis(2-hydroxyethyl)oleanamide].

Large Scale Conversion of Algal Biomass into Fatty Acid Bis(2-Hydroxypropyl)Amide Derivative Fatty acid diisopropanolamide was prepared following the procedure described above for the synthesis of diethanolamide by in situ transesterification followed by amidation method.

A dried biomass (99.5 g, *Chlorella Vulgaris*) yielded 31.65 g of FAMEs which was treated with bis(2-hydroxypropyl)amine (94.95 g) and sodium methoxide (1.59 g) to provide fatty acid bis(2-hydroxypropyl)amide (32.1 g) as a light brown waxy solid. The identity of the products was confirmed by comparing $^1H$ NMR of the product with that of standard amides[N-bis(2-hydroxypropyl)palmitanamide and N-bis(2-hydroxypropyl)oleanamide].

Certain embodiments of the methods and products disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of fatty acid alkanolamide (FAAA) synthesis and isolation from lipid-containing algal biomass, the method comprising:

reacting the lipid-containing algal biomass with an alkanolamine, an alcohol, or a mixture of alkanolamine and alcohol, with or without catalysts, in a reaction solvent to achieve in situ conversion of fatty acyl donors (FADs) in the lipids to FAAA, fatty acid alkyl esters (FAAE), or a mixture of FAAA and FAAE;

recovering the FAAA, FAAE, or mixture of FAAA and FAAE from the reaction medium; and converting any recovered FAAE to FAAA by reacting the recovered FAAE with alkanolamine in a second step.

2. The method of claim 1, wherein the reaction solvent is an alcohol, and the in situ conversion of the FAD in the lipids results in formation of FAAE, the method comprising:

recovering FAAE as a separate phase; and converting the recovered FAAE to FAAA in the second step by reacting the recovered FAAE with alkanolamine.

3. The method of claim 2, wherein the reaction solvent is methanol, and the in situ conversion of the FAD in the lipids results in formation of FAAE comprising fatty acid methyl esters (FAMEs), the method comprising:
   recovering the FAME as a separate phase; and
   converting the recovered FAME to FAAA in the second step by reacting the recovered FAME with alkanolamine.

4. The method of claim 3, wherein the FAMEs are produced through in situ transesterification by reacting the lipid-containing algal biomass directly with a mixture of methanol and an acid catalyst.

5. The method of claim 4, wherein a recyclable solid-acid catalyst is used in the transesterification step.

6. The method of claim 5, wherein the recyclable solid-acid catalyst comprises Amberlyst 15.

7. The method of claim 3, wherein a two-step transesterification-followed-by-amidation with alkanalamides, with or without an amidation-catalyst, is used to recover algal lipids as FAAA products.

8. The method of claim 7, wherein the amidation catalyst is sodium methoxide (NaOMe).

9. The method of claim 7, wherein ethanolamine is used to convert the recovered FAME to fatty acid ethanolamide (FAEA) in the second step.

10. The method of claim 7, wherein diethanolamine is used to convert the recovered FAME to fatty acid diethanolamide (FADEA) in the second step.

11. The method of claim 7, wherein isopropanolamine is used to convert the recovered FAME to fatty acid diisopropanolamide (FADIPA) in the second step.

12. The method of claim 3, wherein the steps are conducted a temperature of less than 120° C.

13. The method of claim 3, wherein at least above 95% of the total lipids in the biomass is recovered as FAAA.

14. The method of claim 3, wherein the recovered FAME is treated with 10 w/w % charcoal and filtered.

15. The method of claim 1, wherein the lipid-containing algal biomass comprises the microalgae strain *Schizochitrium limacinum* or *Chlorella Vulgaris.*

16. The method of claim 1, wherein the lipid-containing algal biomass comprises a heterotrophic unicellular alga.

17. The method of claim 1, wherein the lipid-containing algal biomass comprises an alga which produces high levels of polyunsaturated fatty acids with a rapid growth rate.

18. The method of claim 3, wherein freeze-dried microalgae biomass and Amberlyst 15 are mixed with methanol, and heated at 90° C.

19. The method of claim 18, wherein the Amberlyst 15 is present at about 40% g/g-biomass, and the methanol is present at about 5 mL/g-biomass.

20. The method of claim 1, wherein the reaction solvent is an alkanolamine and the lipids undergo in situ conversion directly to FAAA, the method further comprising recovering the FAAA from the reaction mixture through selective extraction into an immiscible organic solvent, and isolating the recovered FAAA from the organic solvent through distillation of the solvent.

21. The method of claim 20, where the reaction solvent is ethanolamine and the in situ amidation reaction is conducted at a temperature of 120° C. or less, with or without a catalyst.

22. The method of claim 20, where the reaction solvent is diethanolamine and the in situ amidation reaction is conducted at a temperature of 120° C. or less, with or without a catalyst.

23. The method of claim 20, wherein the reaction solvent is diisopropanolamine and the in situ amidation reaction is conducted at a temperature of 120° C. or less, with or without a catalyst.

24. The method of claim 20, wherein the immiscible organic solvent is EtOAc.

25. The method of claim 24, wherein above 90% of the total lipids in the biomass are recovered as FAAA.

26. The method of claim 25, wherein the recovered FAAA is treated with 10 w/w % charcoal and filtered to improve the color of the final product.

* * * * *